United States Patent [19]
Verbiest et al.

[11] Patent Number: 5,719,502
[45] Date of Patent: Feb. 17, 1998

[54] ESD MONITORING CIRCUIT AND DEVICE

[75] Inventors: Noel Verbiest; Lyle Nelsen; Steven B. Heymann, all of San Jose, Calif.

[73] Assignee: Noux Corporation, San Jose, Calif.

[21] Appl. No.: 587,256

[22] Filed: Jan. 17, 1996

[51] Int. Cl.$^6$ .................. G01R 29/12; G01N 27/60
[52] U.S. Cl. .......................... 324/457; 324/452
[58] Field of Search .................. 324/452, 454, 324/455, 457, 72

[56] References Cited

U.S. PATENT DOCUMENTS

| | | | |
|---|---|---|---|
| 3,824,454 | 7/1974 | Stern et al. | 324/457 |
| 3,851,247 | 11/1974 | Vosteen et al. | 324/72 |
| 3,857,066 | 12/1974 | Cline et al. | 324/454 X |
| 4,520,318 | 5/1985 | Hascal et al. | 324/457 |
| 5,054,325 | 10/1991 | Dechene et al. | 324/454 X |
| 5,508,607 | 4/1996 | Gibson | 324/121 R |
| 5,600,251 | 2/1997 | Akiyama | 324/457 |
| 5,608,326 | 3/1997 | Mucci et al. | 324/454 |

OTHER PUBLICATIONS

Sedra et al., "Microelectronic Circuits", 1982 (month unavailable), pp. 71–73, 1982.

*Primary Examiner*—Glenn W. Brown
*Attorney, Agent, or Firm*—The Kline Law Firm

[57] ABSTRACT

An electrometer that is able to measure the potential difference of an electrostatically charged body without causing a rapid discharge of the subject charge. The electrometer has an input impedance that is in excess of 100 gigohms. The input impedance is created by an active voltage divider. The active voltage divider is a unique circuit which instead of the typical voltage divider that utilizes a passive resistive divider and an op amp in a voltage follower configuration, uses an amplifier configuration that attenuates its input signal. One result of this configuration is that the input line can then be guarded. This allows the device to be supplied with probes that are not subject to typical elements of degradation of the input signal with distance from the circuit, e.g. parasitic capacitance and bandwidth limitations. The device operates with two channels: a first channel recognizes the presence of a charged body in the proximity of the device, while the second channel measures the magnitude of the potential difference on a charged body examined by a probe. The device includes alarms that are activated when charge levels exceed a chosen level. A display tower allows a user to visually demonstrate to trainees the magnitude of ESC events.

27 Claims, 33 Drawing Sheets

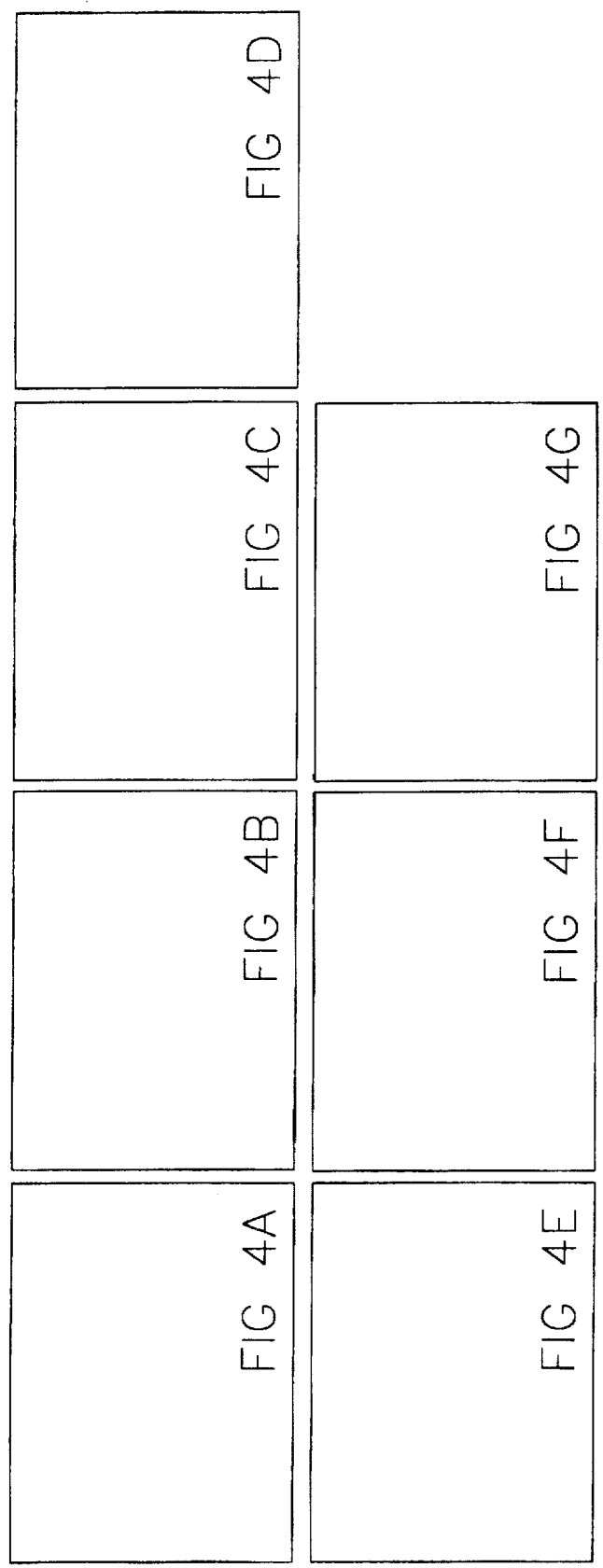
FIGURE 4 MULTI SHEET PLACEMENT KEY

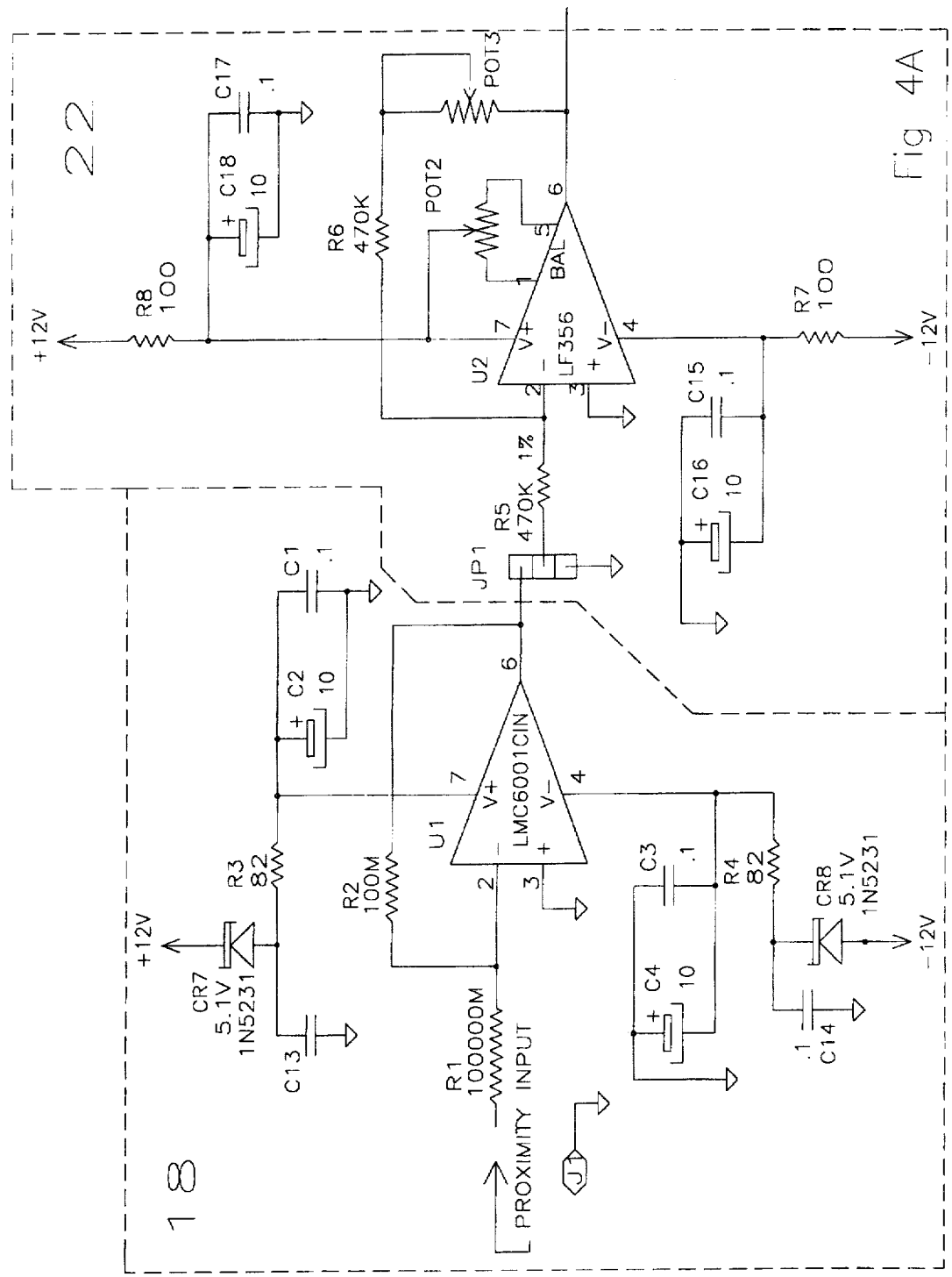

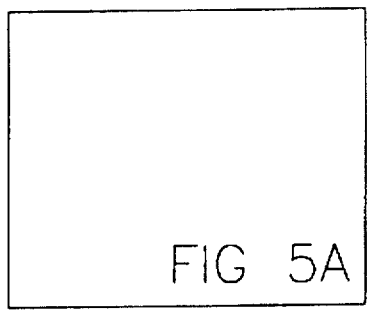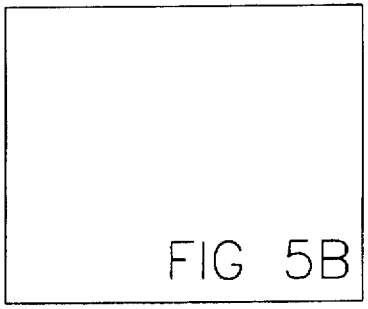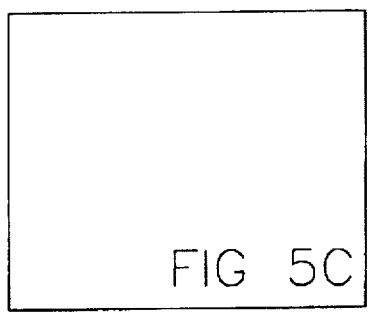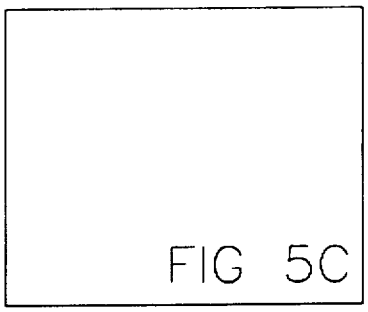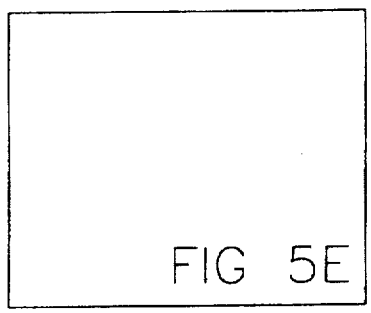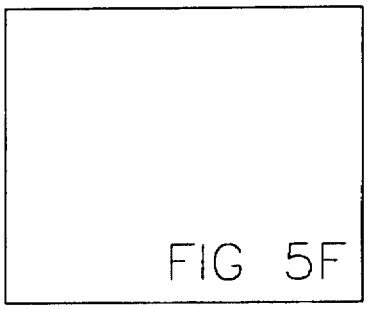
FIGURE 5 MULTI SHEET PLACEMENT KEY

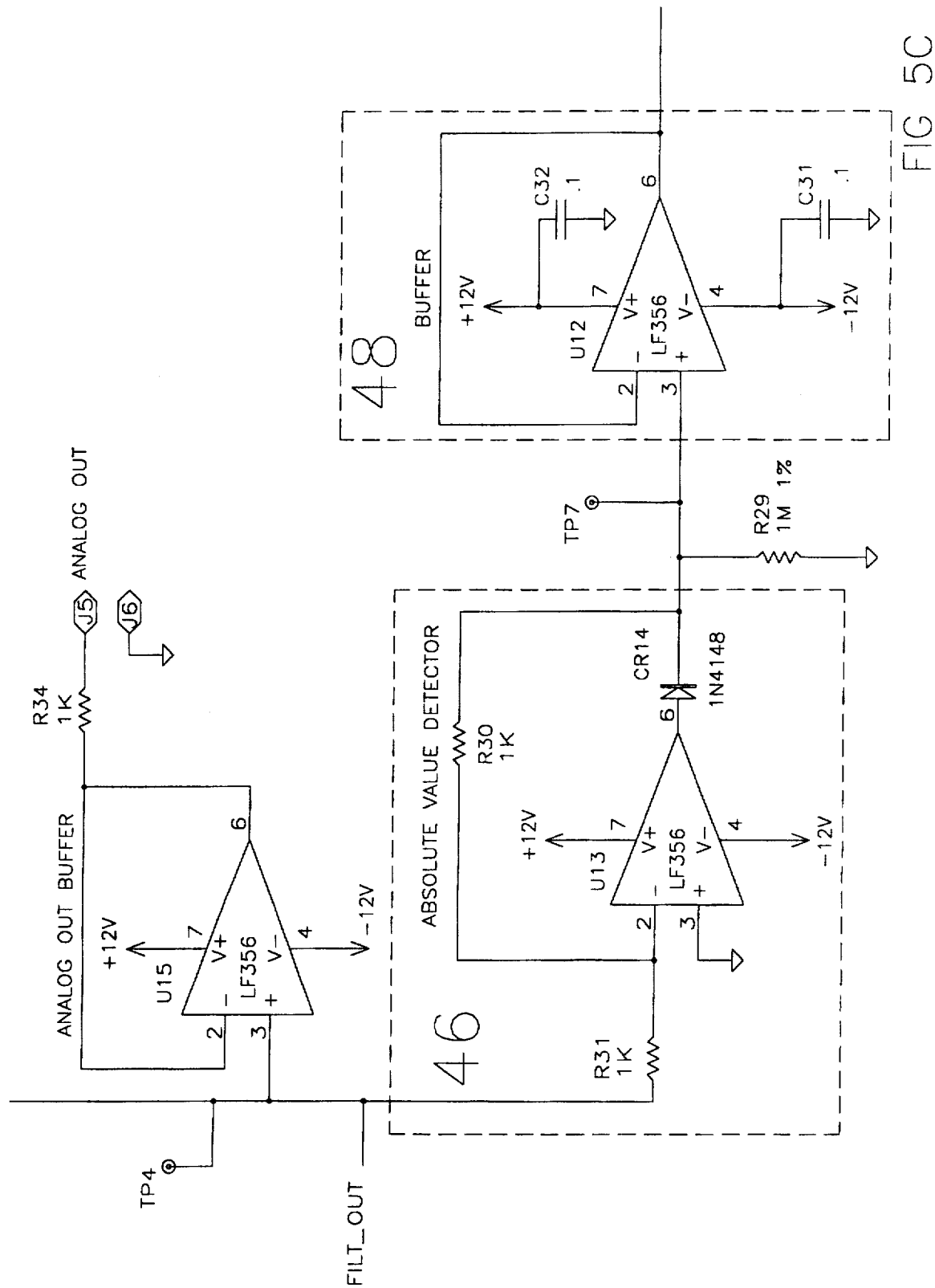

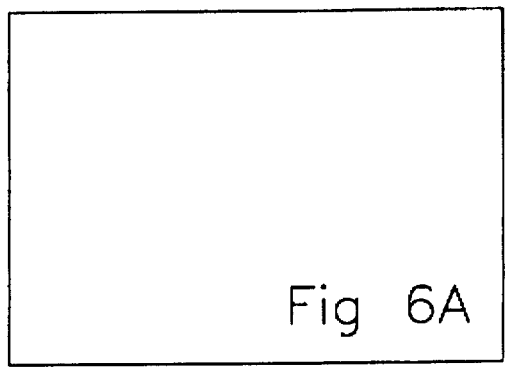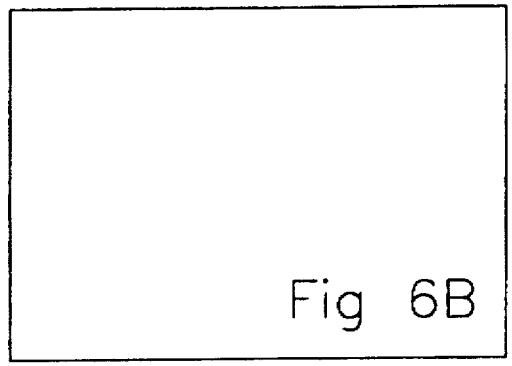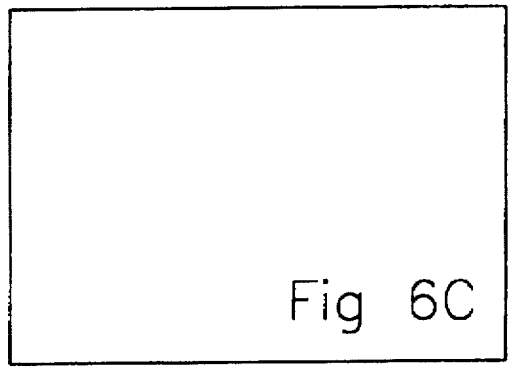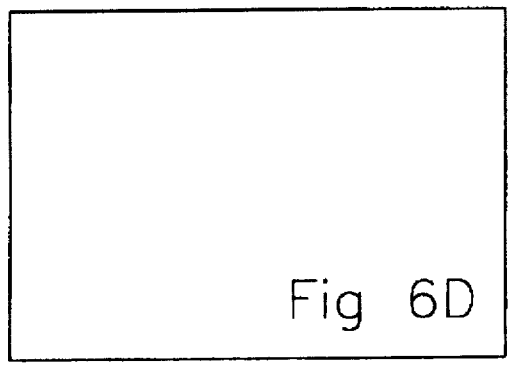
FIGURE 6 MULTI SHEET
PLACEMENT KEY

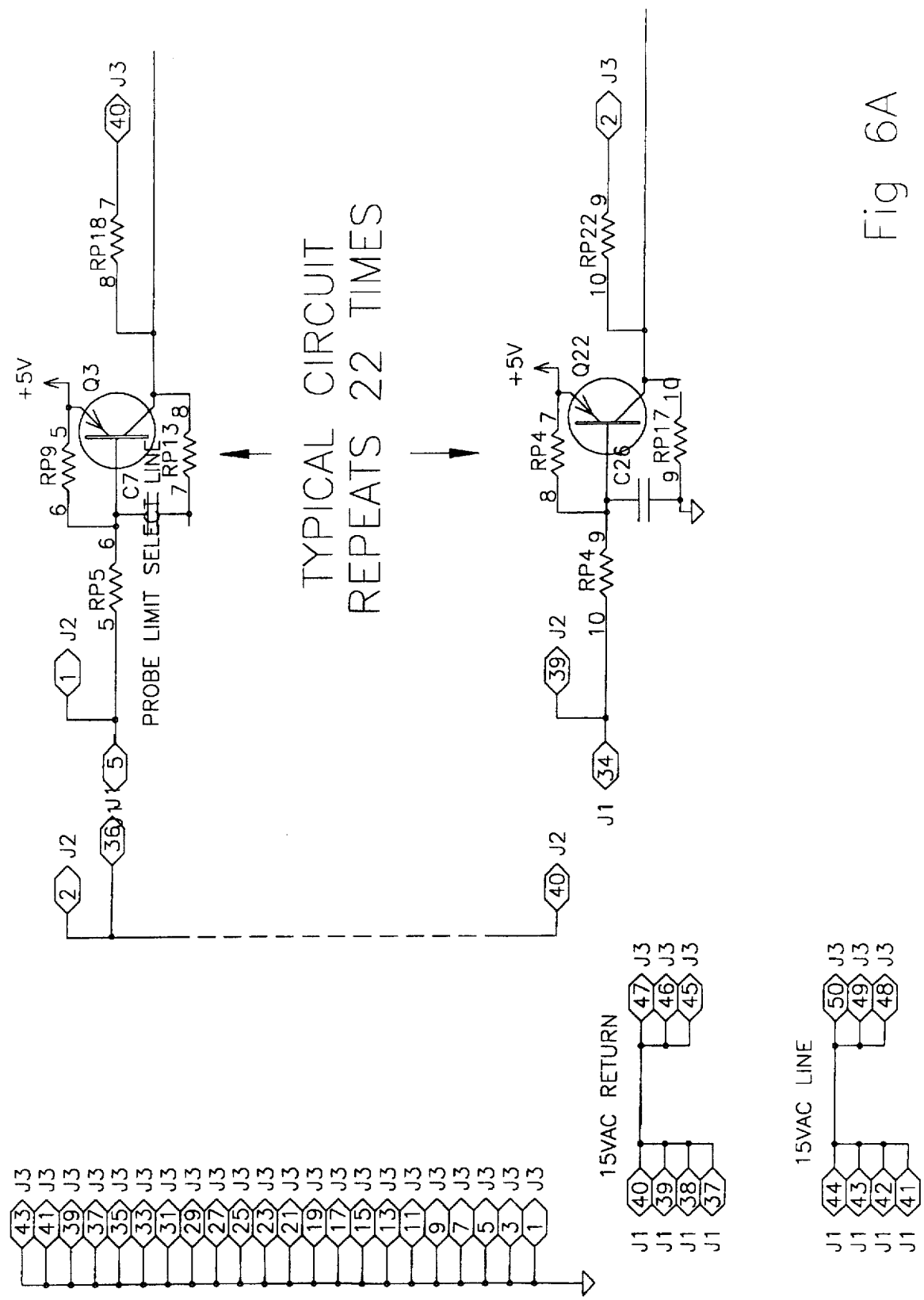

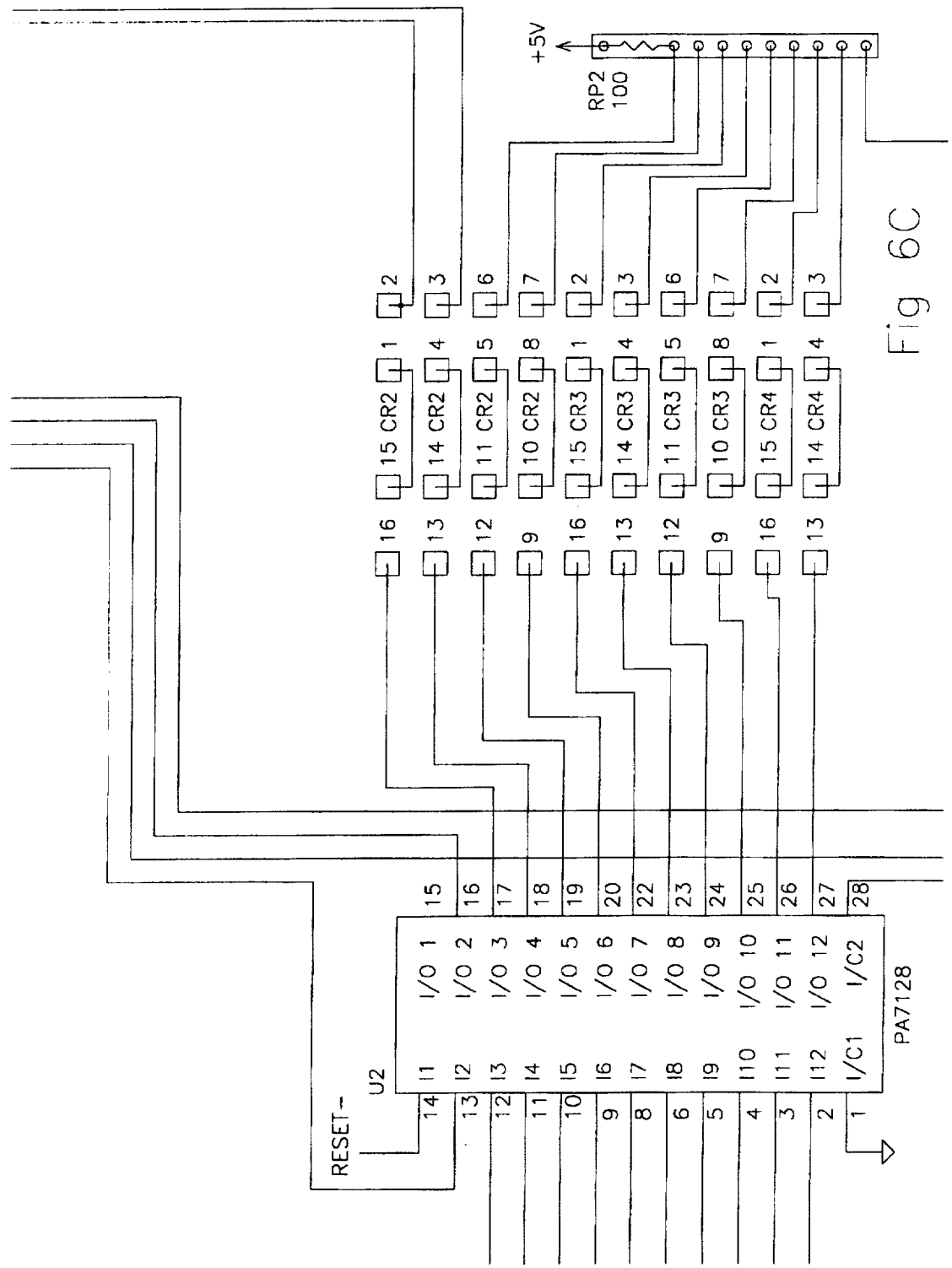

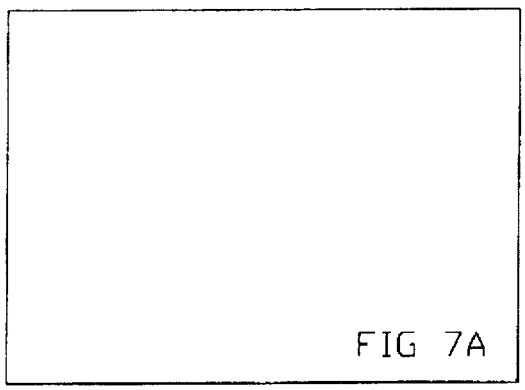
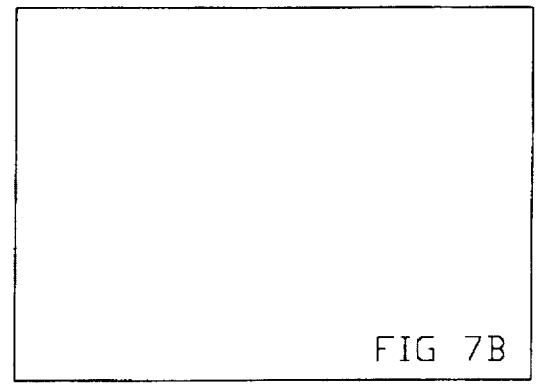
FIGURE 7 MULTI SHEET PLACEMENT KEY

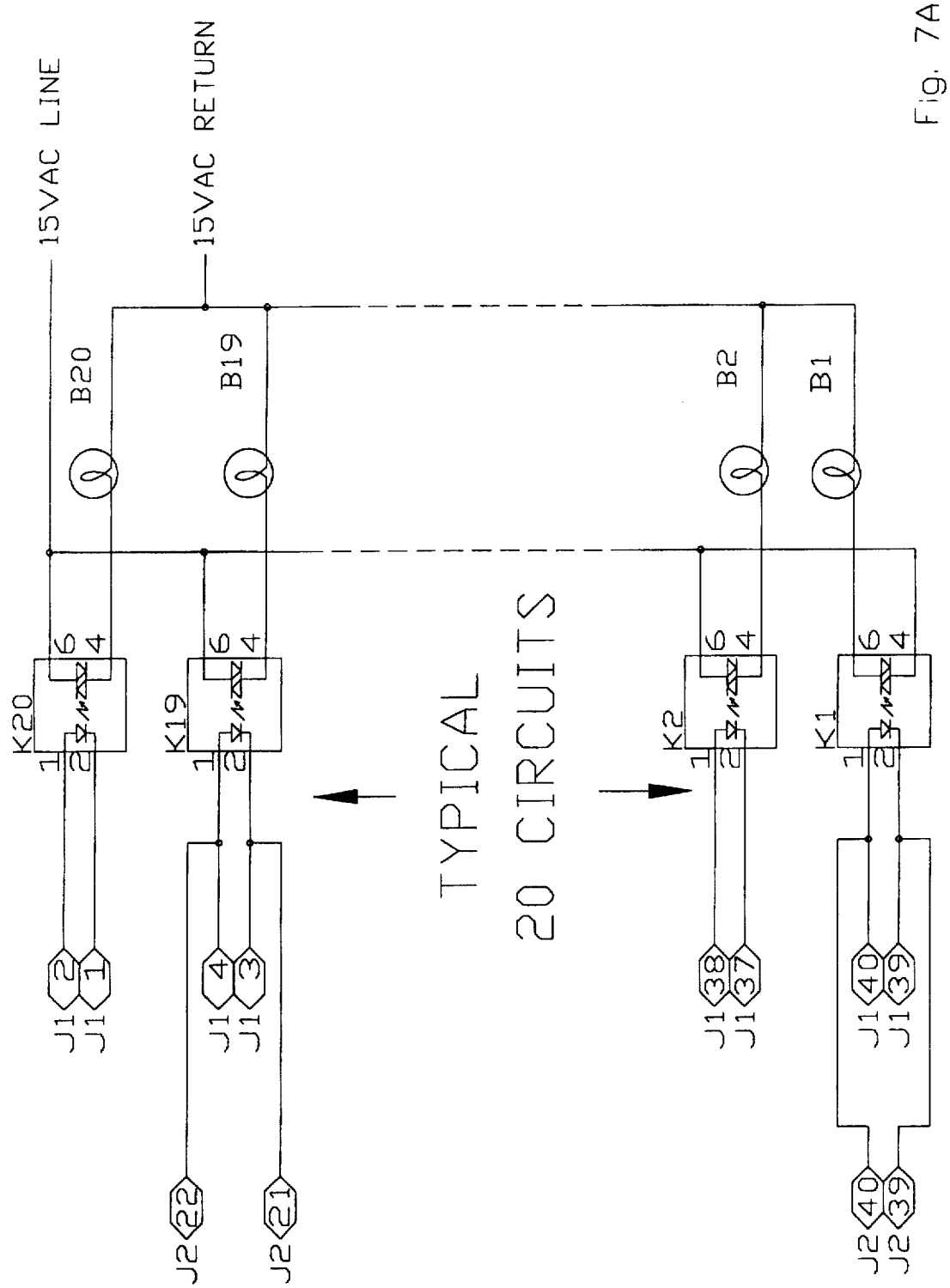

FIGURE 9 MULTI SHEET PLACEMENT KEY

ESD MONITORING CIRCUIT AND DEVICE

FIELD OF THE INVENTION

The present invention relates generally to electronic monitoring devices, and more particularly is a device to measure electrostatic charges.

BACKGROUND OF THE INVENTION

One of the most insidious problems in electronics manufacturing is that of electrostatic charge (ESC) and its frequently destructive companion, electrostatic discharge (ESD). A body, including a human body, in its neutral state has as many electrons as it has protons. If that body loses or gains electrons, the body will become positively or negatively charged. There are a number of mechanisms by which a body can acquire and lose electrons, and thus become "charged". Three of those mechanisms are summarized below.

Triboelectrification, or contact electrification, occurs when two materials come into contact with each other and then separate. One of the materials will extract electrons from the second material at the moment of separation so that the first material is then negatively charged, while the second material is positively charged.

A second type of charging is induction charging. This occurs when a neutral conducting body is brought into the electric field of a charged body, creating charge polarization in the conducting body. If the conducting body is momentarily grounded while it is still under the influence of the electric field, a neutralizing charge will be drawn from the ground, thus neutralizing the charge polarization. When the connection to ground is broken and the conducting body is moved outside the reach of the electric field, the conducting body will retain a net charge opposite in polarity to that of the charged body. A practical example of induction charging occurs when a charged human body passes in close proximity to a PCB which happens to be lying on an insulated surface, such as a workbench, with an edge of the PCB very close to a grounded wire or other grounded conducting structure. As the human body passes the PCB, the electric field will cause charge polarization to occur in the PCB. If the secondary electrical field associated with the charge polarization is strong enough, arcing may occur between the edge of the PCB and the grounded wire. As the human body moves away from the PCB, the PCB will retain a net charge, which, in turn, may cause a second ESD if not handled properly.

A third type of charging is conduction charging. Conduction charging occurs when two conductive bodies, one charged and a second one neutral, are brought into electrical contact, either because the bodies are making galvanic contact or because an arc occurs between the bodies. The charge in the first body will be redistributed across both bodies. An example of conduction charging is when a charged human touches an isolated conducting object, such as a PCB. Some portion of the charge in the human body will flow into the PCB, and, depending on the magnitude of the initial charge in the human body, an arc may or may not occur between the PCB and a fingertip of the human.

In practice, although there are other mechanisms by which a body can acquire a charge, the three types of charging described above are those occurring most frequently in industry. The true charging mechanism occurring in a particular instance is sometimes very difficult to pinpoint, and may well be a combination of all three mechanisms. For example, a person wearing conductive shoes and walking over an insulating surface, such as a carpet, will cause triboelectrification between the shoe soles and the carpet. However, if that same person wears insulating shoes, then the body will charge due to a combination of triboelectrification between the bottom of the shoes and the carpet and induction charging between the top of the shoe soles and the feet of the person.

Three quantities are frequently used to describe an ESC situation. They are Potential Difference (V), the Coefficient of Self Capacitance, commonly referred to as Capacitance (C), and the amount of charge (Q). These quantities are related by the equation $Q=C \times V$. For example, the shoe soles of a person walking over a carpet, will cause extraction of a charge Q which is deposited into body capacitance C, causing the Potential Difference V of the body to rise in the amount $V=Q/C$.

The amount of charge extracted at each sole-carpet interaction depends on numerous variables such as the contamination of the carpet, humidity, materials involved, size of the foot, weight of the person, and many others. Q is highly variable, it is also difficult to measure. The typical charge transferred during an average sole-surface interaction amounts to 5–20 nanoCoulomb/cm$^2$, a typical sole surface for a pair of shoes being on the order of 100 cm$^2$.

Neither is a person's capacitance a constant. Capacitance depends on the surface area of a person's skin, the position of the body, especially the feet, with respect to the surface, and many other factors. The capacitance of a person walking over a carpet changes continuously and is fairly unpredictable. This capacitance is very difficult to measure. A typical value for an average adult, standing motionless, would be between 100 and 200 picoFarads.

The potential V, being equal to Q/C, will thus vary widely with each shoe sole to surface interaction, and with each change of the position of the body. Practically, values of 1–20 kilovolts, of both polarities, are quite common. It is relatively easy to measure this Potential Difference.

OBJECTS, SUMMARY, AND ADVANTAGES OF THE INVENTION

Accordingly, it is an object of the present invention to provide a means to measure the Potential Difference of an electrostatically charged body, while avoiding an abrupt ESD event.

It is a further object of the present invention to provide a means to display the magnitude and polarity of the potentials measured.

It is a still further object of the present invention to provide a display method that is easy for a user to comprehend.

In summary, the present invention is an electrometer that is able to measure kilovolt level potentials which are commonly found on electrostatically charged bodies, without rapidly draining away the charge that gave rise to the potential. The electrometer has an input resistance in excess of 100 gigaohms, far higher than that of known electrometers. The electrometer uses an active voltage divider in its input stage. The active voltage divider is a unique circuit which, instead of the traditional resistive voltage divider followed by an op amp in the voltage follower configuration, uses an op amp with resistive feedback such that the circuit attenuates the input signal by an amount fixed by the ratio of two resistor values. The overall accuracy of the electrometer is basically determined by this ratio, not by the absolute value of the resistors, and can therefore be made to measure very accurately. One result of this input configuration is that the input terminal of the op amp is a "virtual ground". This allows the input line to be very simply guarded, in the strict sense of that term.

The device operates with two channels: a first channel recognizes the occurrence of a charge event in the proximity of the device, while the second channel measures the magnitude of a subject charge examined by a probe. The device includes alarms that are activated when charge levels exceed a chosen level. A display tower allows a user to visually demonstrate to trainees the magnitude of ESC events.

An advantage of the present invention is that the device can be used to measure a large range of potentials.

Another advantage of the present invention is that the ability to shield the input to the circuit allows the possibility of a remote probe assembly, without degrading the performance of the electrometer.

Still another advantage of the present invention is that the effect of parasitic capacitance is eliminated, thereby greatly increasing the bandwidth of operation of the device.

A further advantage of the present invention is that it displays the magnitudes of measured charges in a logarithmic scale.

A still further advantage of the present invention is that it allows the input line to be guarded, thereby enabling more flexibility in the probe to be used with the device.

These and other objects and advantages of the present invention will become apparent to those skilled in the art in view of the description of the best presently known mode of carrying out the invention as described herein and as illustrated in the drawings.

BEST MODE OF CARRYING OUT THE INVENTION

Figure 1:
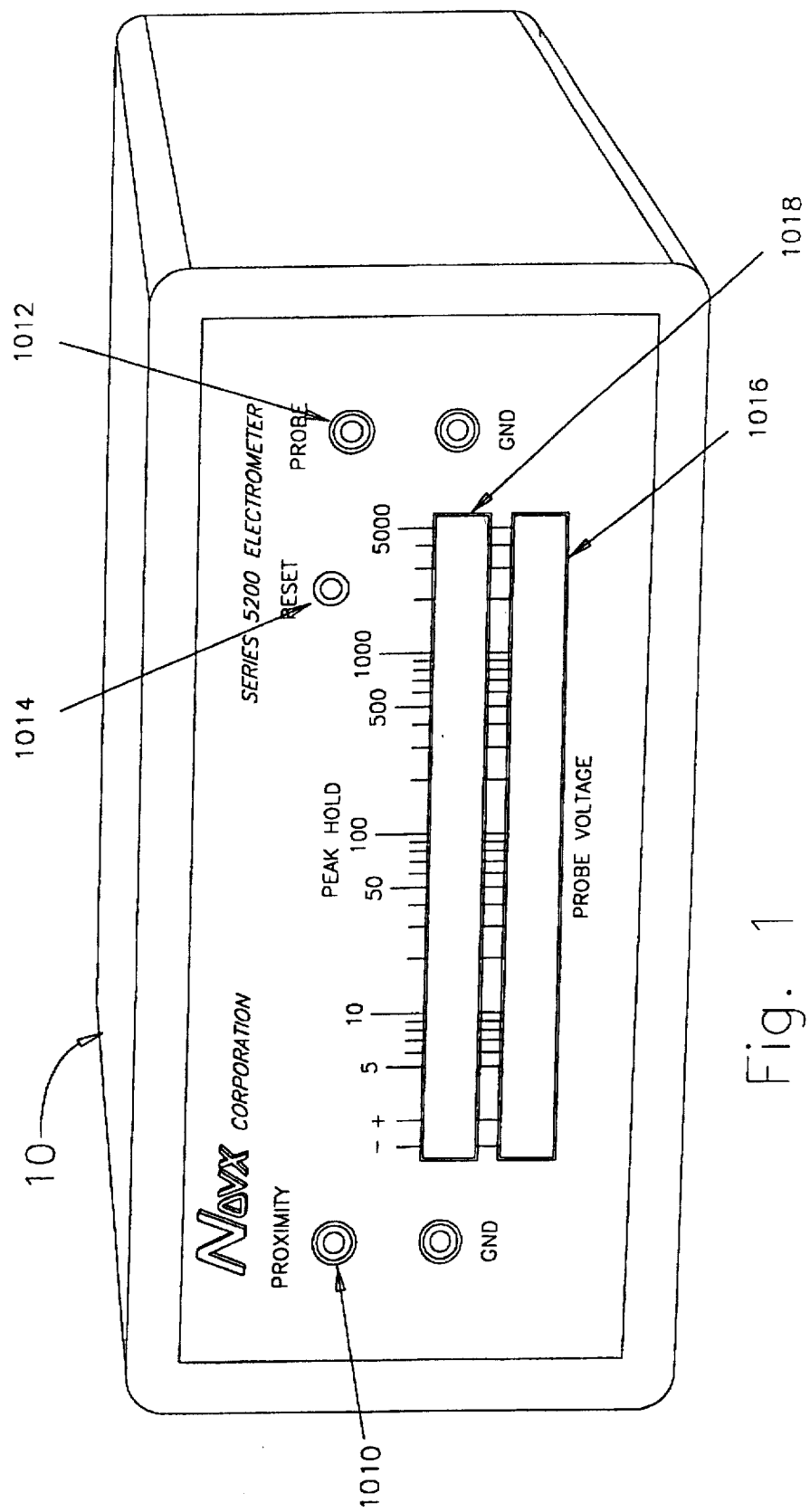
FIG. 1 is a perspective view of the electrometer of the present invention.
Figure 2:
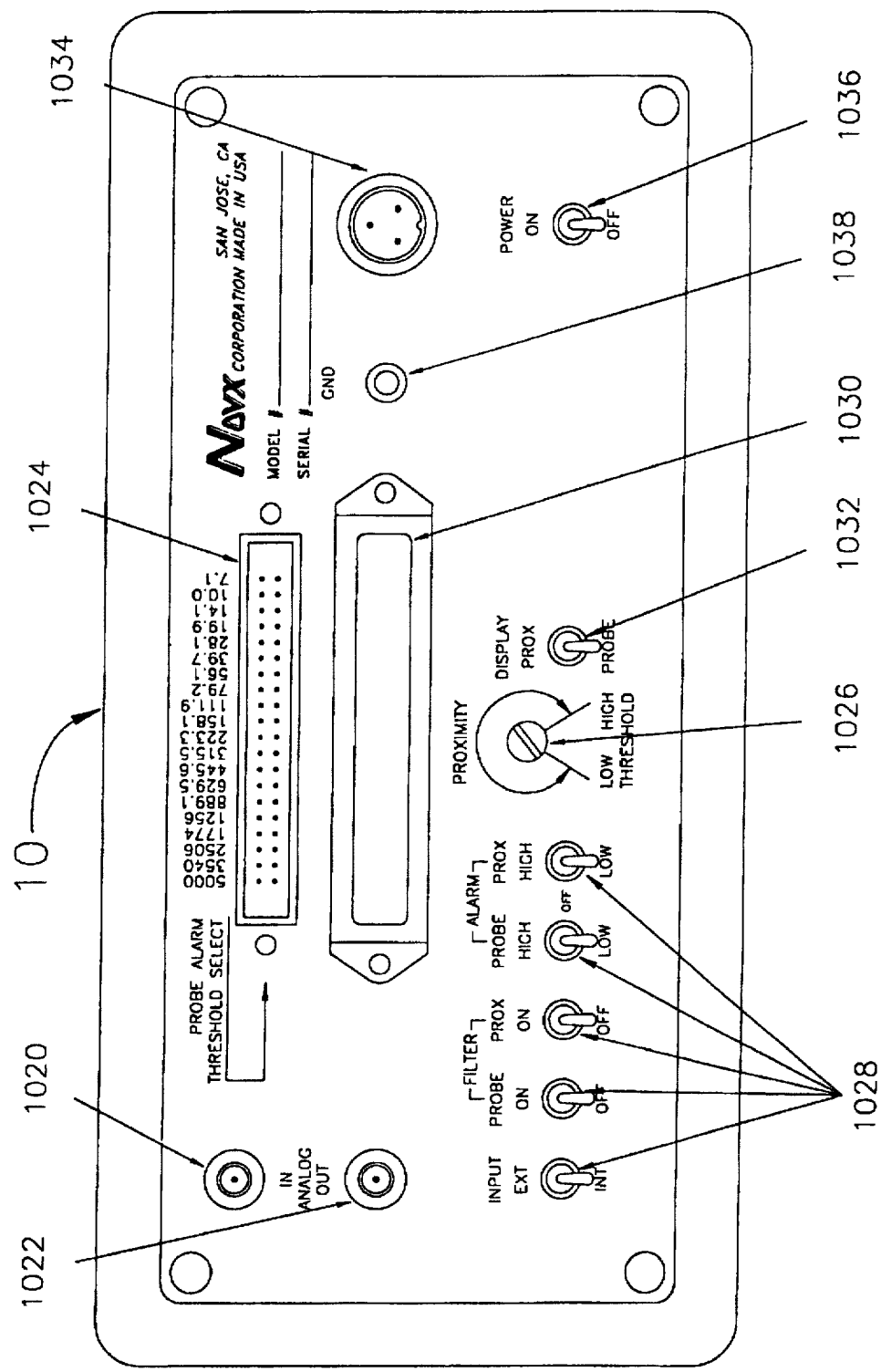
FIG. 2 is a rear view of the electrometer of the present invention.
Figure 3:
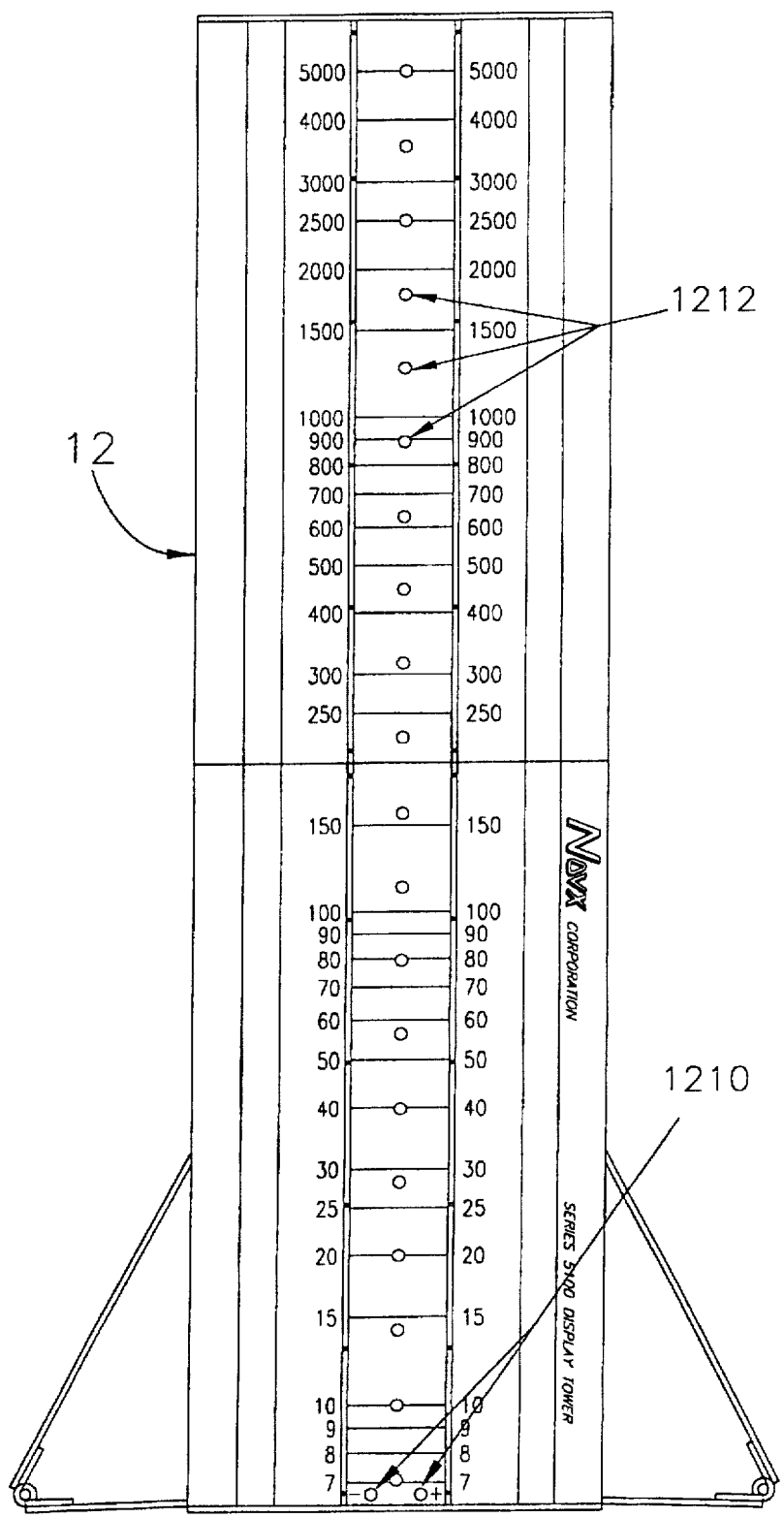
FIG. 3 is a perspective view of the display tower.
Figure 4B:
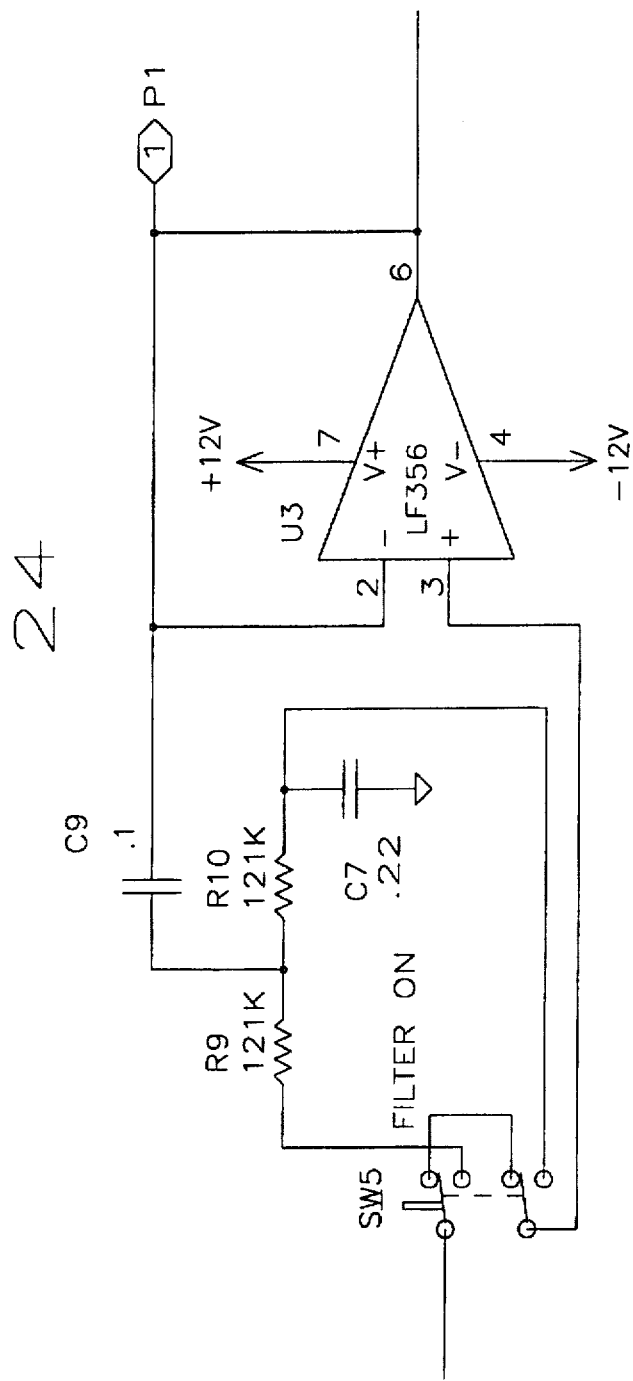
FIG. 4 is a key to FIGS. 4A–14G which comprise a circuit diagram of a first segment of the main PCB of the present invention.
Figure 4C:
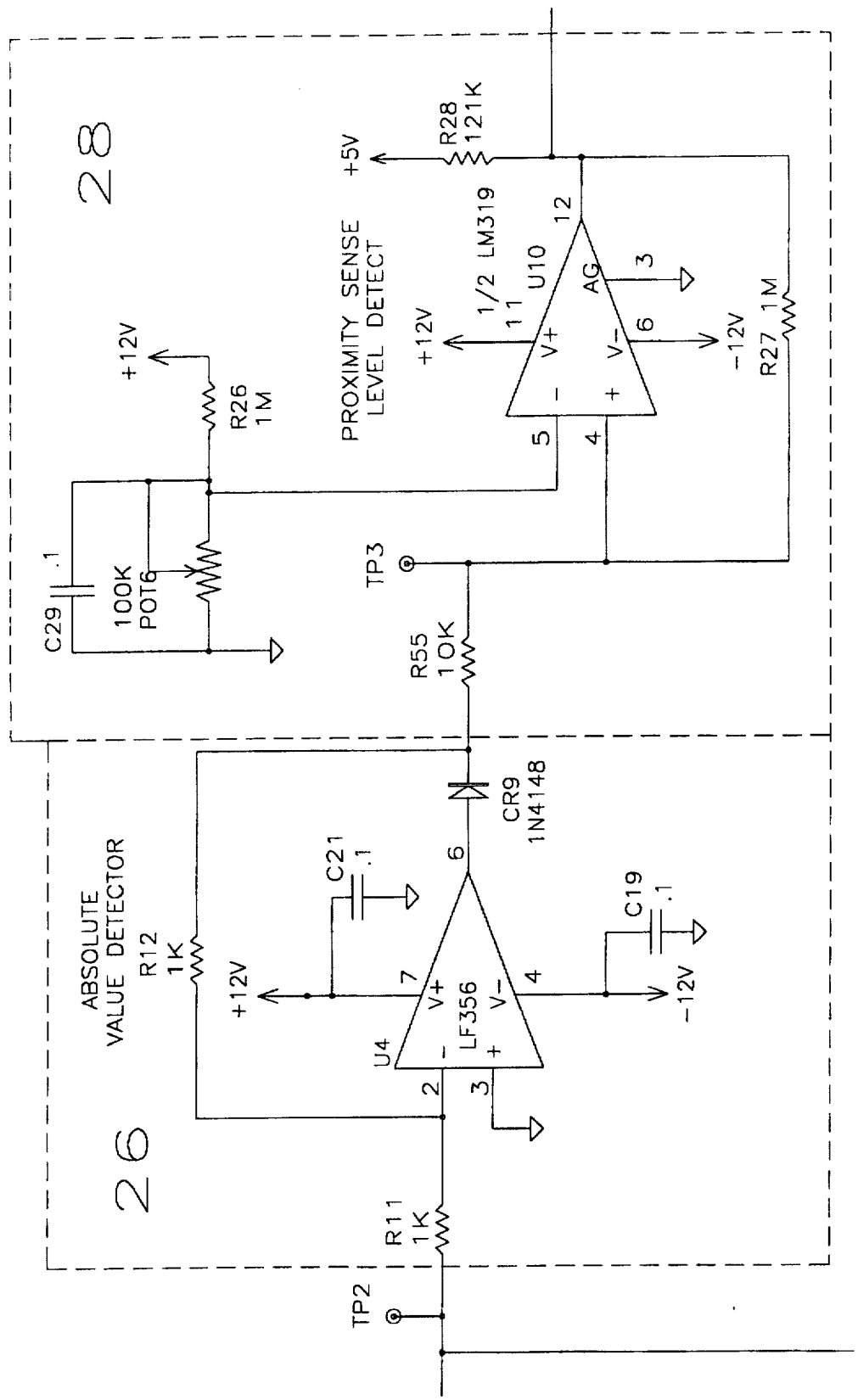
Figure 4D:
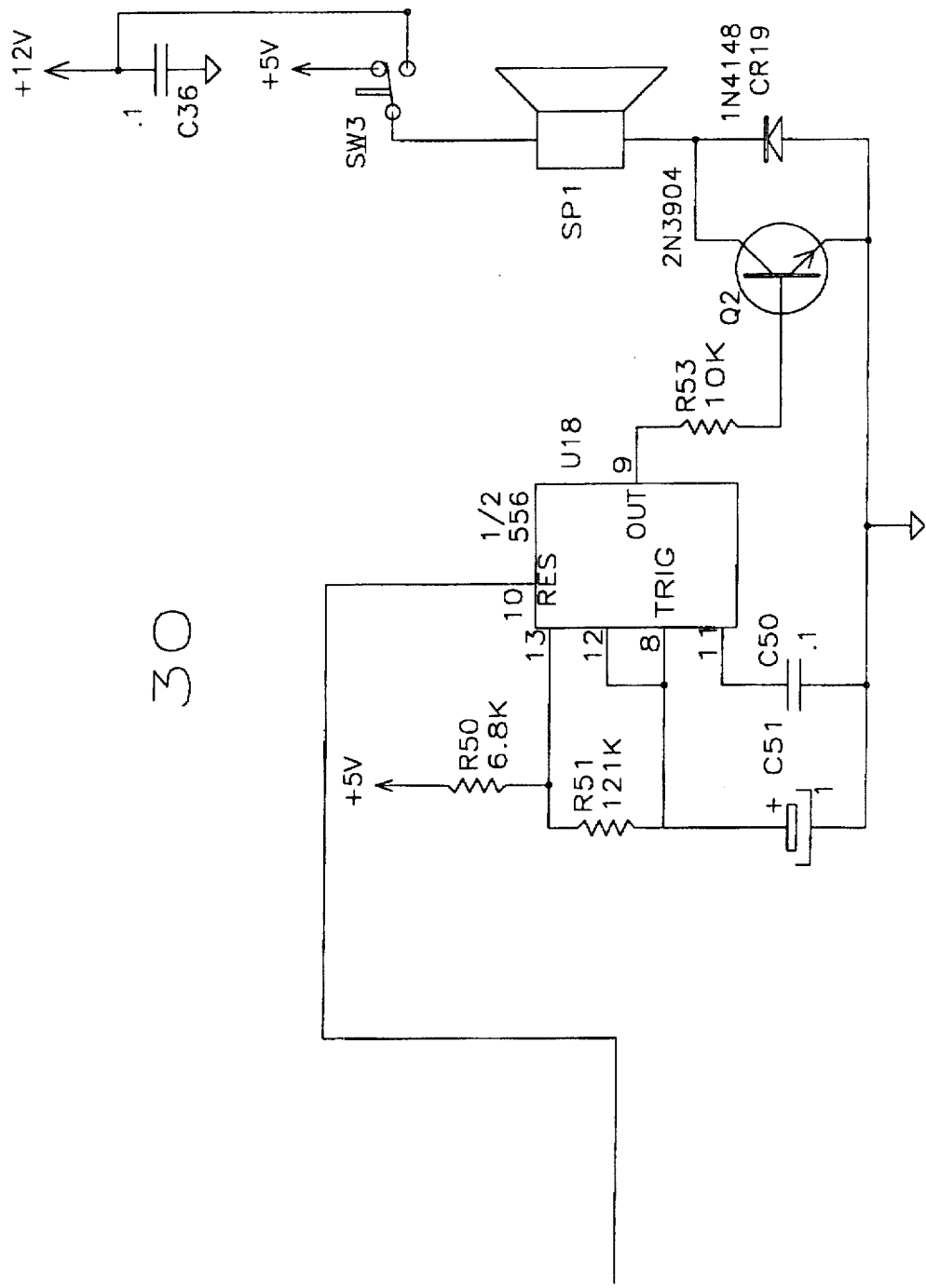
Figure 4E:
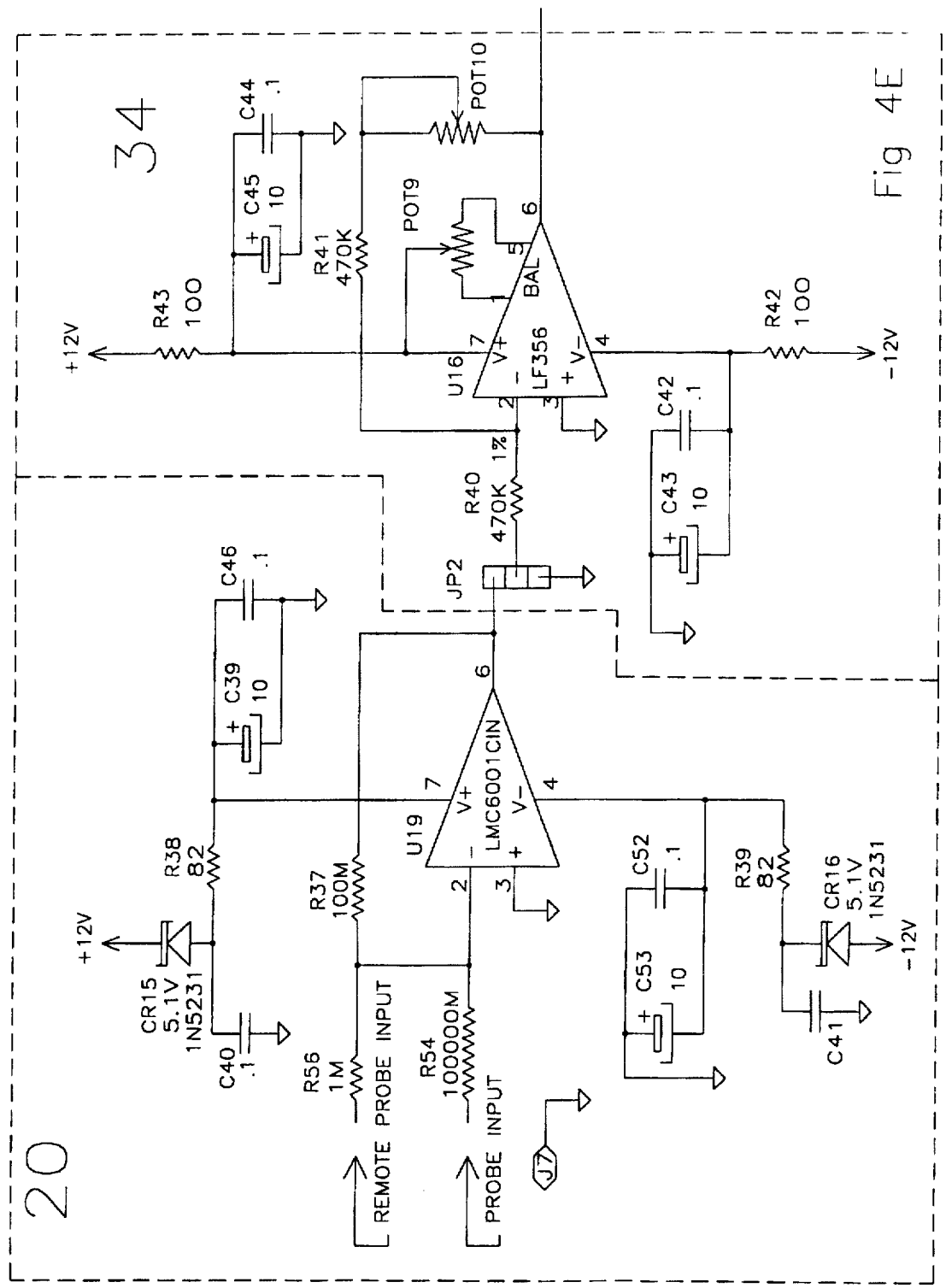
Figure 4F:
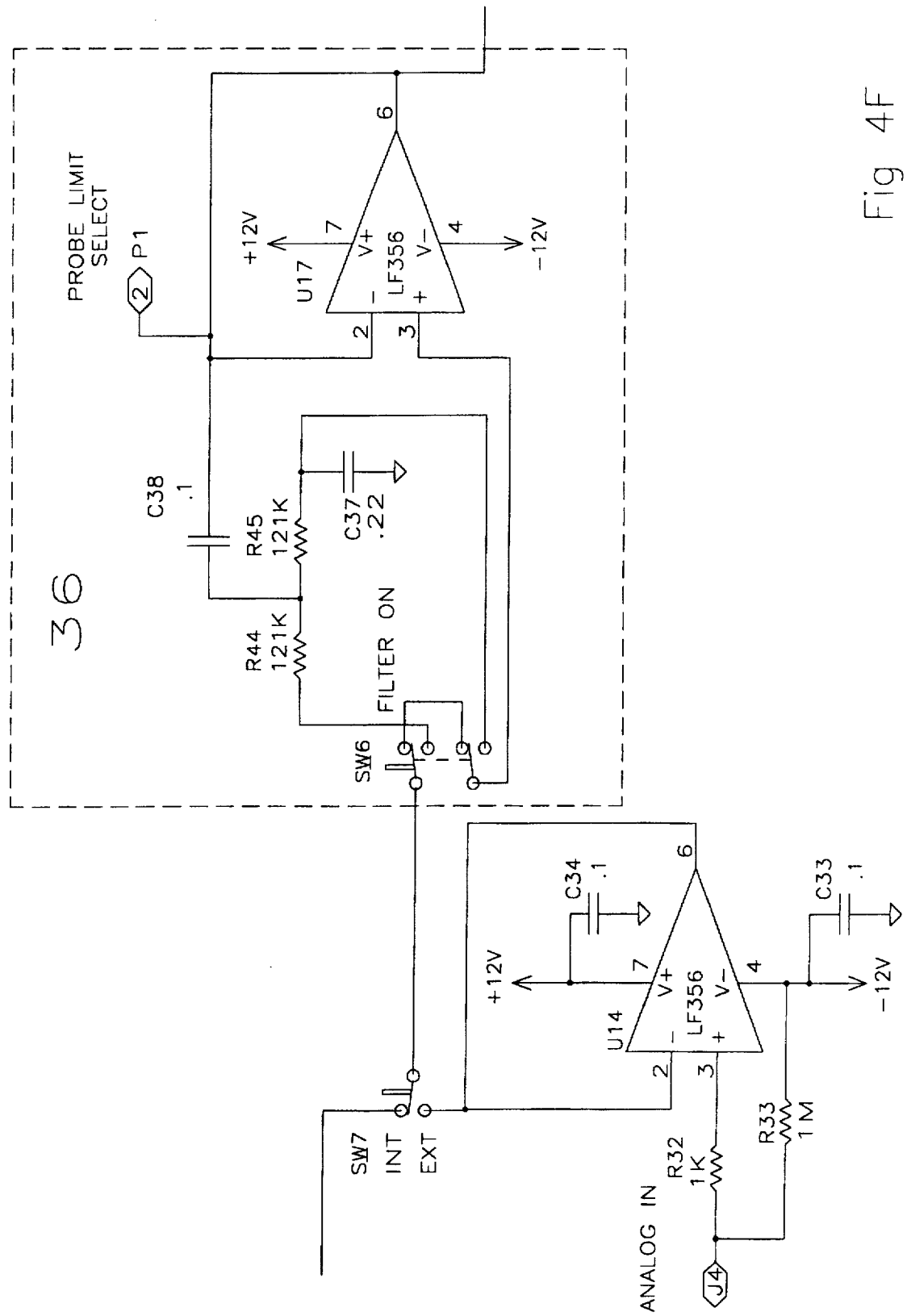
Figure 4C:
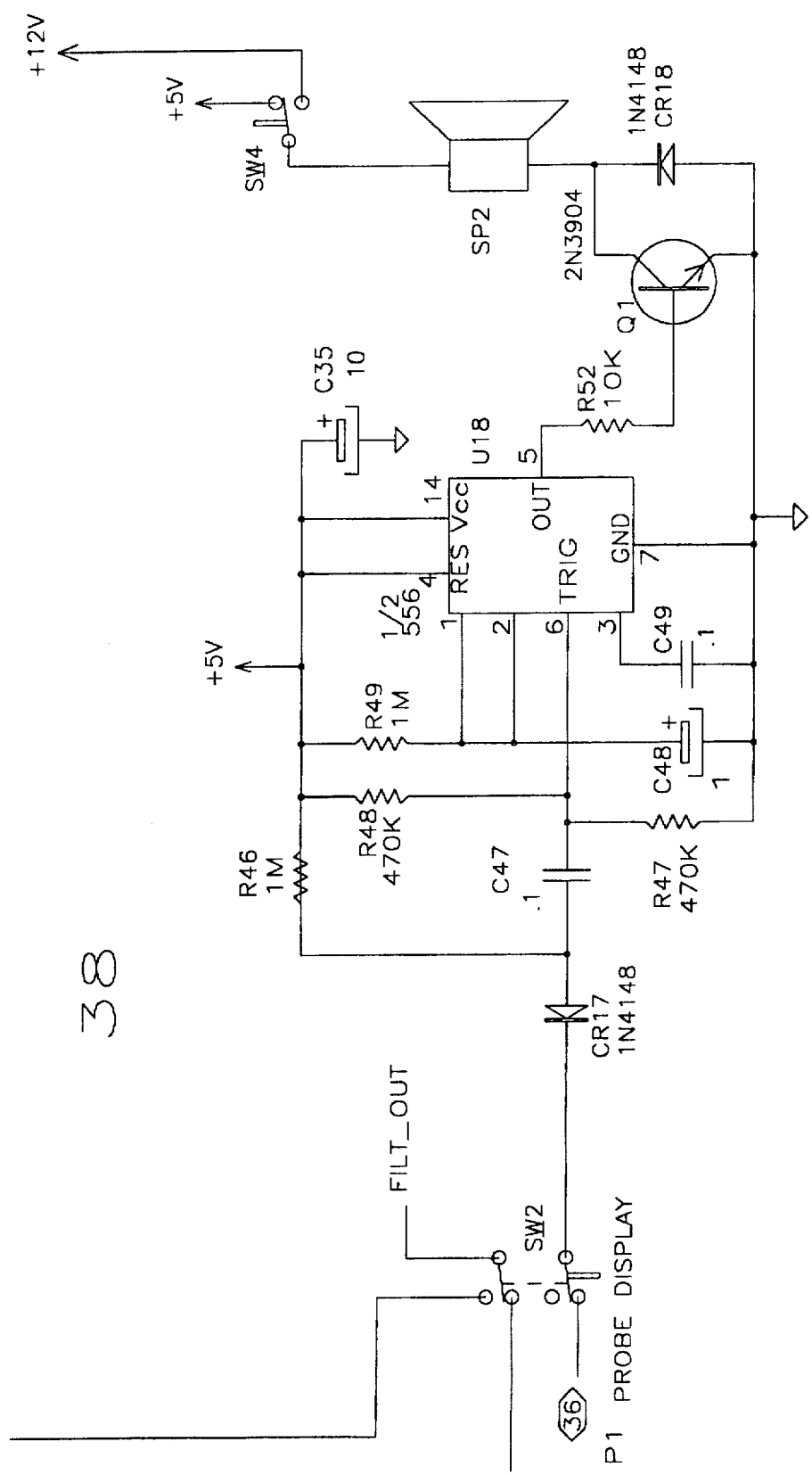
Figure 5A:
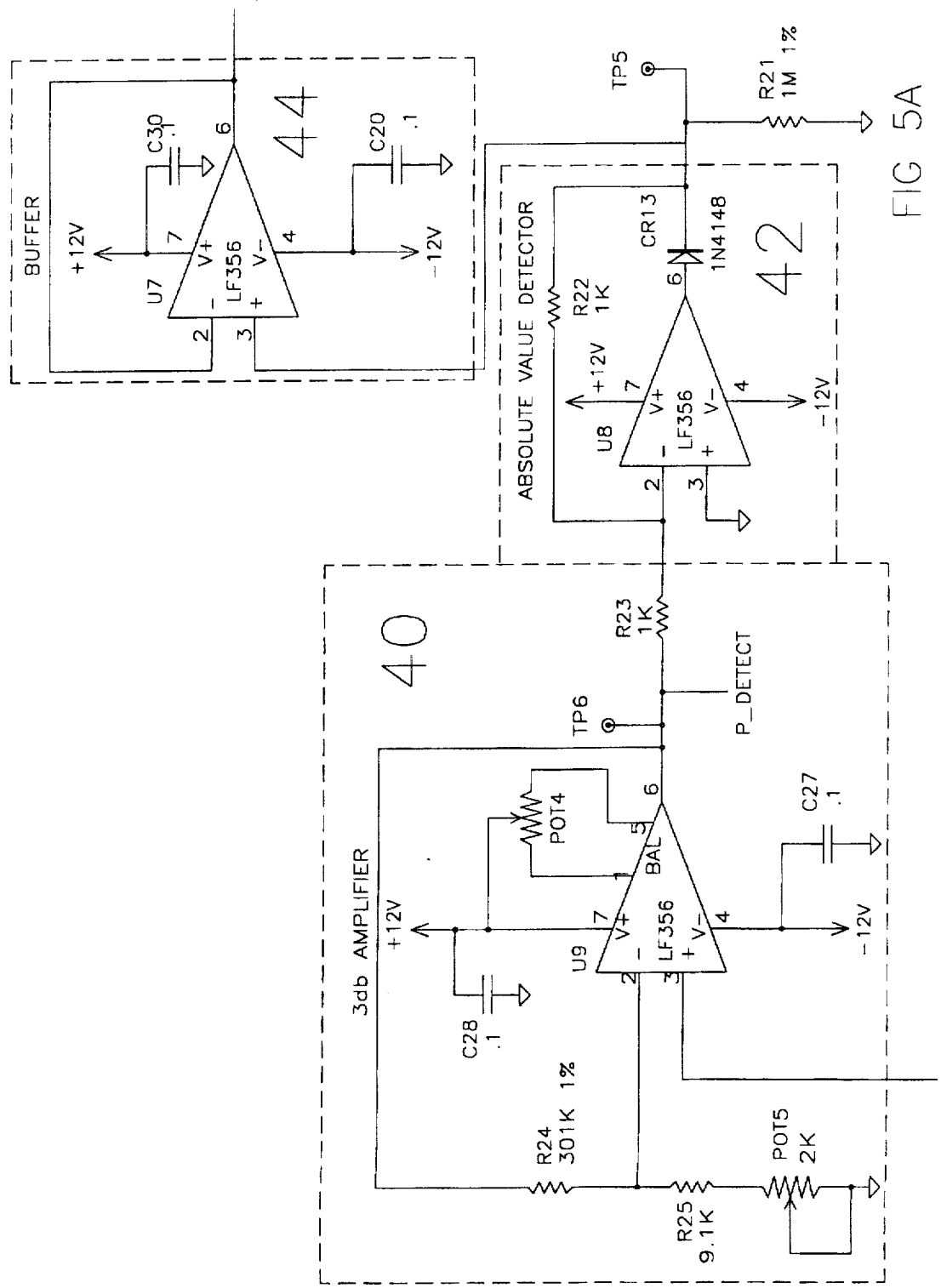
FIG. 5 is a key to FIGS. 5A–5F which comprise a circuit diagram of a second segment of the main PCB of the present invention.
Figure 5B:
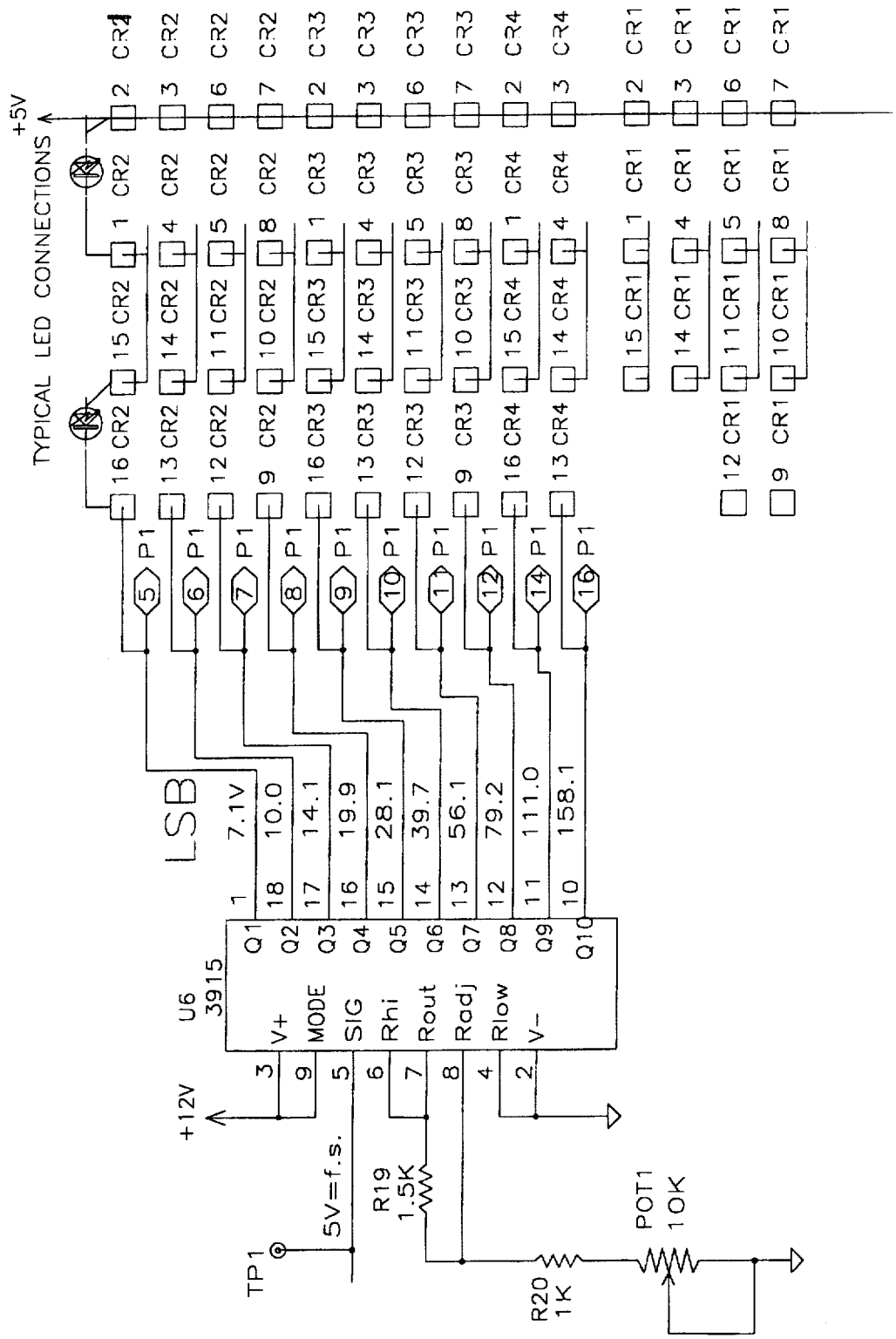
Figure 5D:
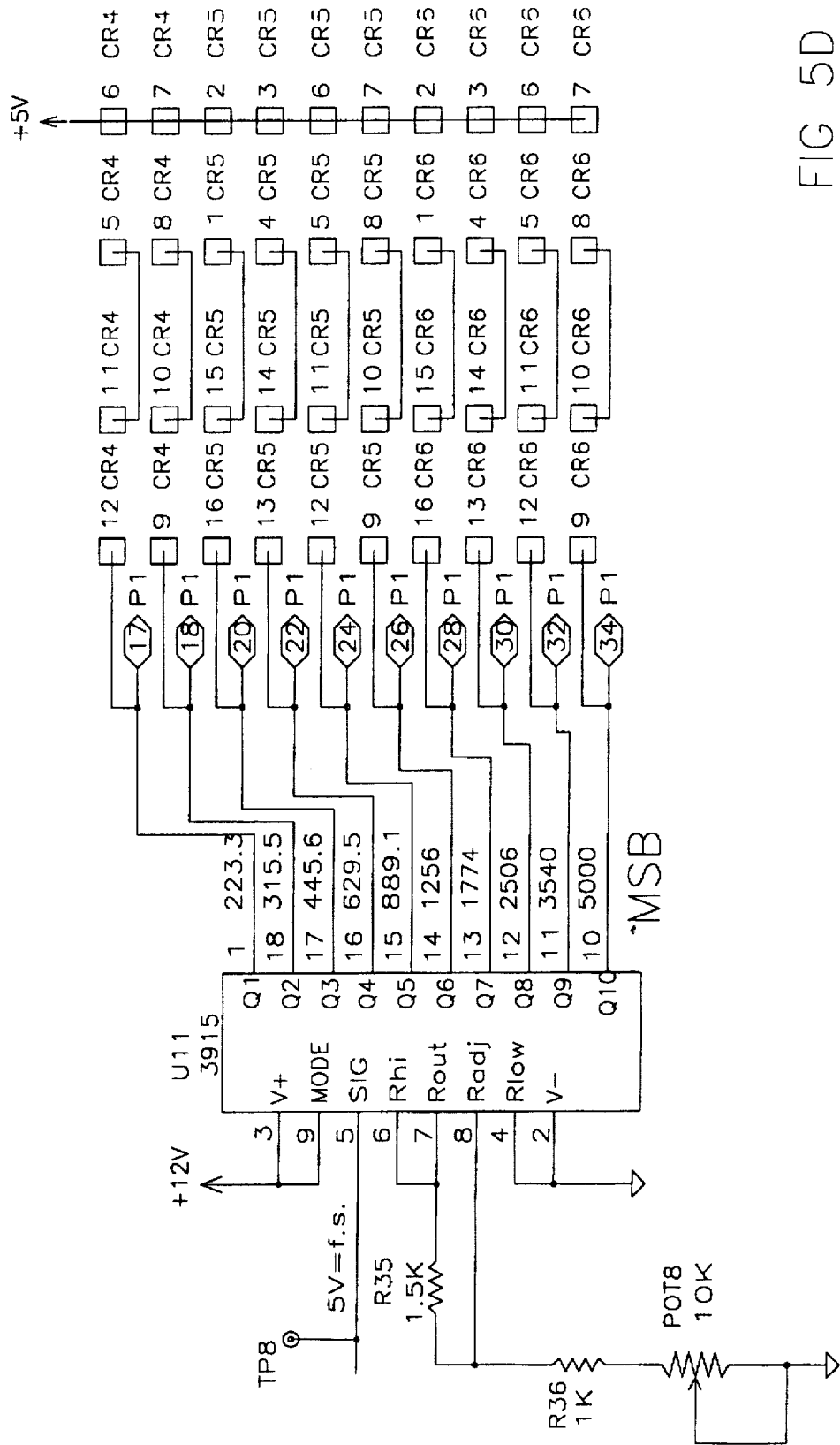
Figure 5E:
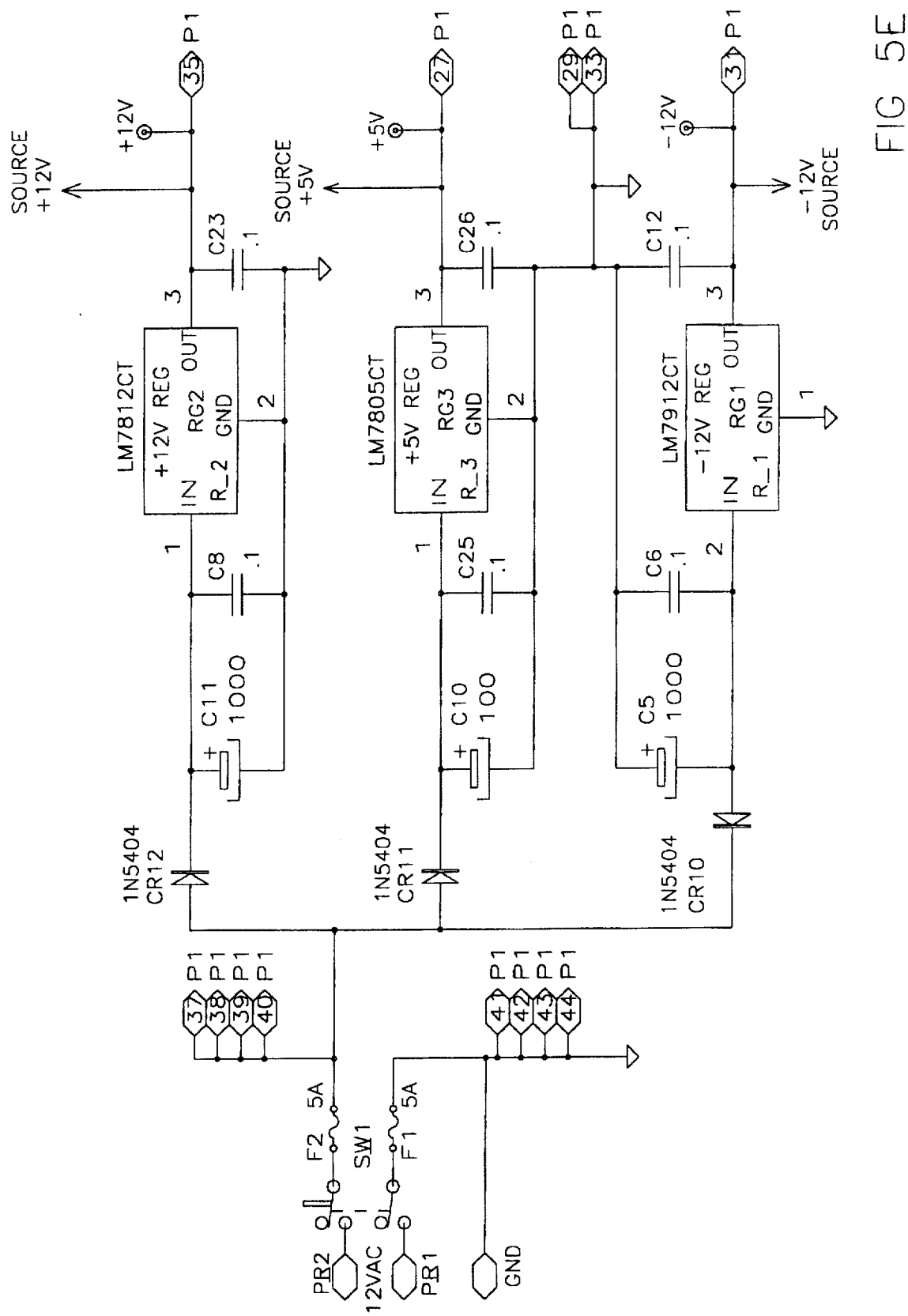
Figure 5F:
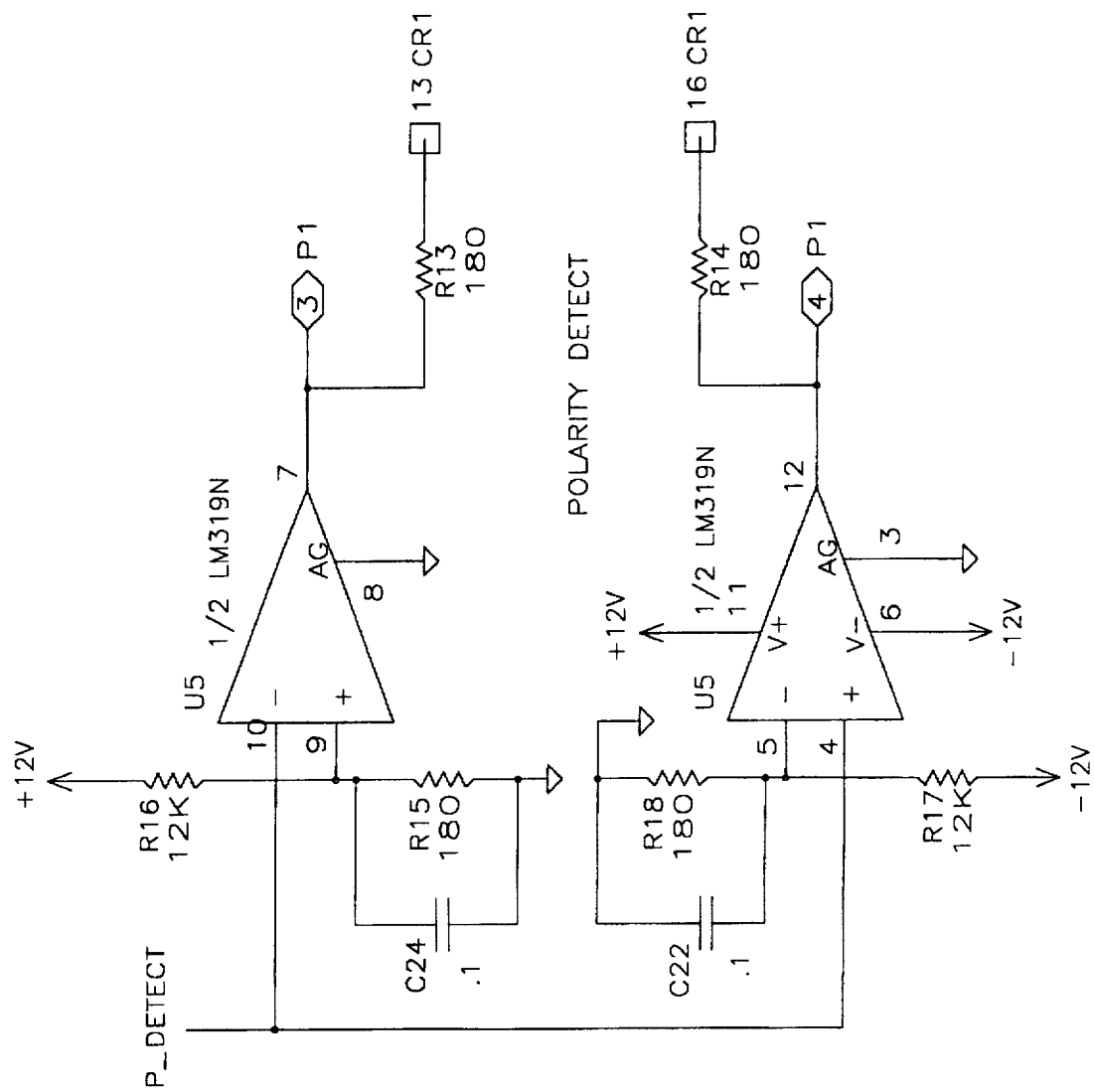
Figure 6B:
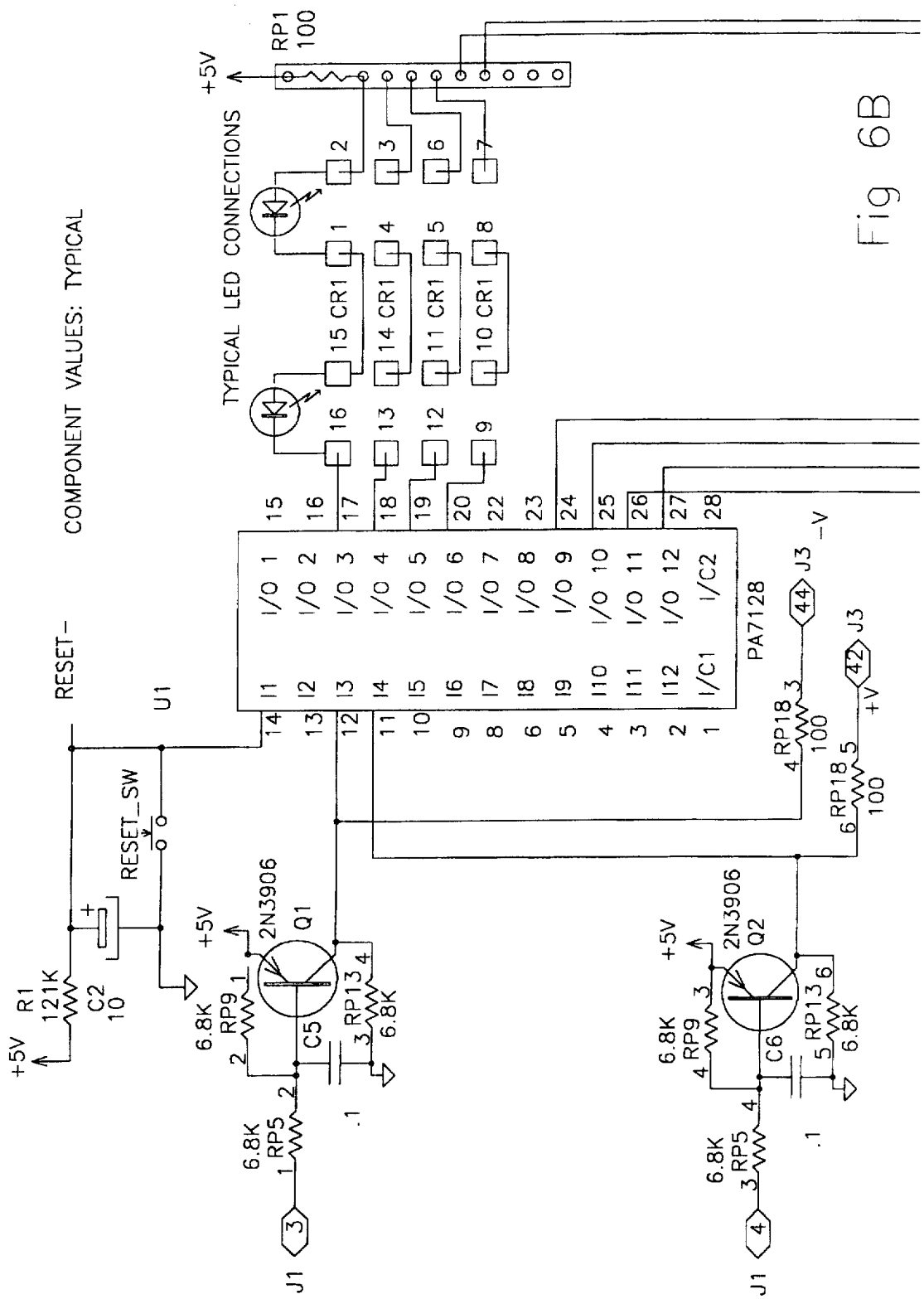
FIG. 6 is a key t FIGS. 6A–6D which comprise a circuit diagram of an optional PCB with the display tower drive circuits and the peak-hold circuits.
Figure 6D:
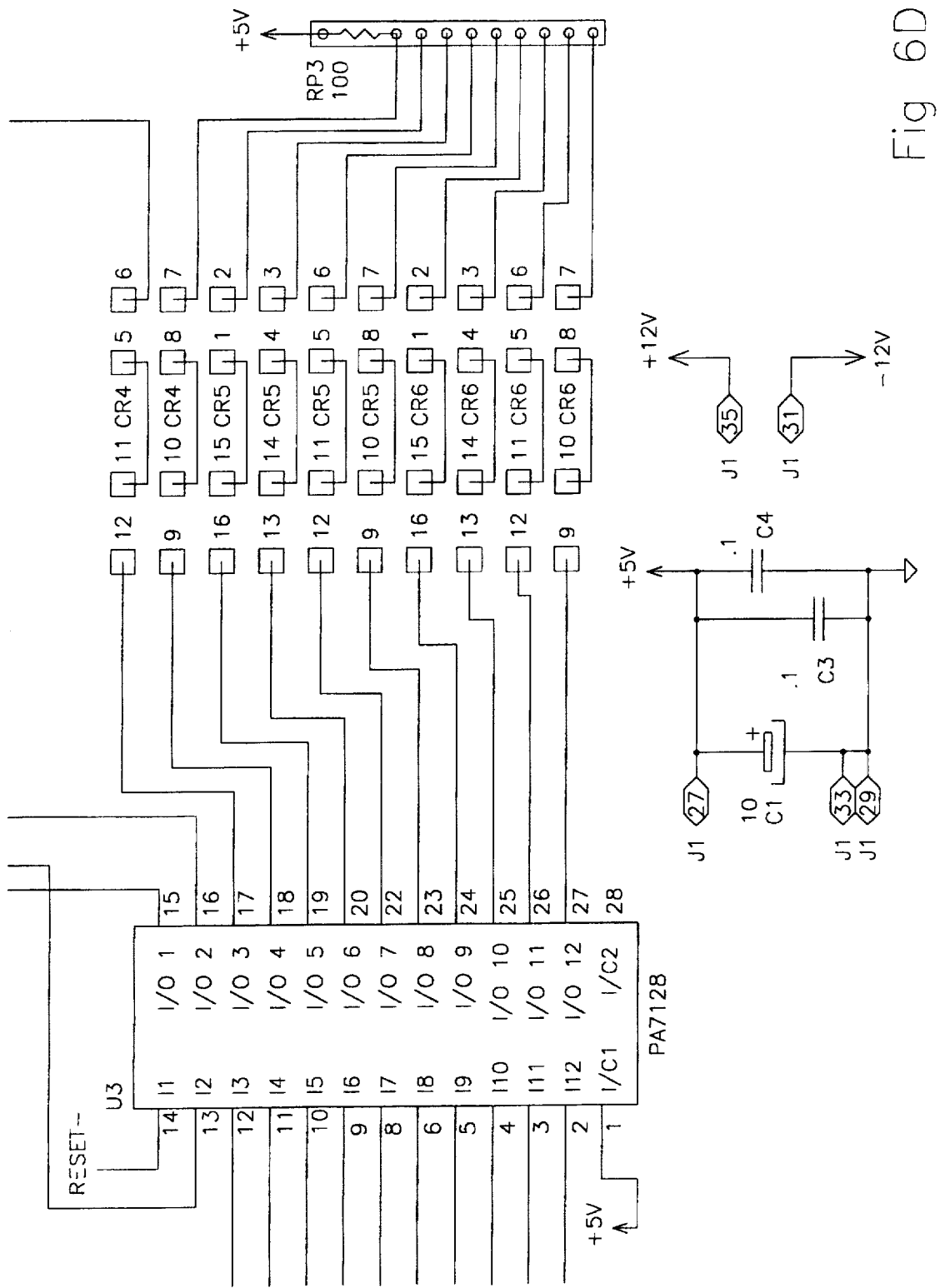

Referring first to FIGS. 1–3, the present invention is an electrometer 10 with an optional visual display tower 12. The front panel of the electrometer 10 includes means for a proximity detect channel input 1010, (typically utilizing an antenna), and a means for a probe channel input 1012. A reset button 1014 is provided to return the peak hold circuit to its zero state. A series of LED's form a logarithmic bar graph display 1016 to indicate the magnitude of the potential being measured. An analogous series of LED's is used for the peak hold indicator 1018.

The rear panel of the electrometer 10 further includes means for an analog input jack 1020 to accommodate other instruments. The device also includes an analog output jack 1022 to provide a means to transmit measured values to a recording device such as a strip chart recorder, an oscilloscope, or other device.

Means are provided to select the alarm threshold for both the probe channel setting 1024 and the proximity detect channel setting 1026. A series of switches 1028 controls the activation of the switched portions of the circuit, and hence the various options available to the user. In the preferred embodiment, the options include means to choose external or internal input, set alarms on or off and high or low, and a means to choose the analog in 1020 or the probe channel 1012.

The rear panel also includes a connection means 1030 to provide communication with the display tower 12. A display selection toggle switch 1032 allows the user to select either input for display, either the proximity detect channel 1010 or the probe channel 1012. The rear panel also includes a connection means 1034 to allow connection of a low voltage power source, a power on/off switch 1036, and a banana jack 1038 for connection to chassis ground.

The display tower 12 includes a set of polarity indicator lights 1210, and a set of voltage indicator lights 1212 which form a logarithmic bar graph display equivalent to LED display 1016. Incandescent light bulbs are used as the indicator lights in the display tower 12 in the preferred embodiment. The number of lights that are activated is of course proportional to the strength of the potential difference being measured.

Referring now to FIG. 4A–4G each of two input channels, a proximity detect channel and a probe channel, of the device are composed respectively of a first active voltage divider 18 and a second active voltage divider 20. The active voltage dividers 18 & 20 give the device an extremely high input impedance of 100 gigohms. This allows the electrometer 10 to measure the potential difference of the charged body without causing a rapid discharge.

As opposed to the traditional configuration of an op amp in a voltage follower configuration, the voltage dividers utilize an op amp in a configuration such that input voltage is attenuated rather than amplified. Referring to the first active voltage divider 18, whose structure is equivalent to the second active voltage divider 20, resistors R1 and R2 are installed in the configuration shown in FIG. 4A–4G. R1 is in the input path to the inverting input terminal of op amp U1, and R2 is in parallel to U1, with a first electrical contact to the inverting input terminal of U1, and a second electrical contact to the output of U1. With this configuration, the attenuation achieved by the voltage divider 18 is equal to R2/R1. In the preferred embodiment, the value of R2 is 100 megohms, and the value of R1 is 100,000 megohms. This gives the active voltage divider an attenuation factor of 0.001, which means that voltage inputs in the range of 0–5 kilovolts are reduced to a range of 0–5 volts. This signal range is far easier to process and measure. A further benefit of the structure of the active voltage dividers is that it allows the input of the circuits to be guarded.

Referring now to FIGS. 4A–4G and 8, after the signal in the proximity detect channel is attenuated by the first active voltage divider 18, it is passed through a first inverter 22, where the polarity of the signal is reversed. The signal is then optionally passed through a first filter 24, after which it is fed to a first absolute value detector 26. If the user desires to display the magnitude of the signal on either the electrometer front panel or the display tower, the signal at this point is fed to the probe channel. (See below, in discussion of probe channel operation.)

In the first absolute value detector 26, the signal in the proximity detect channel is given a positive polarity, regardless of the polarity of the input signal. The output signal of the first absolute value detector 26 of course retains the same magnitude as the input signal.

This signal is then examined in a first comparator 28 to determine the magnitude of the signal. If the magnitude is greater than a preset value, the signal activates a first alarm 30. This alerts a user to the fact that there has been an ESC phenomenon of magnitude exceeding the chosen level in the area.

Referring now to FIGS. 4A-4G and 9A-9C, a signal in the probe channel is attenuated by the second active voltage divider 20. The signal is then passed through a second inverter 34, where the polarity of the signal is reversed. The signal is then optionally processed through a second filter 36. The second filter 36 also includes a switching means SW7 to accommodate an analog signal input means so that an external analog input signal can be accepted. This allows a user to utilize the electrometer's display and recording capabilities with other instrumentation.

The signal from the second filter 36 can be used to activate a second alarm 38. The second alarm 38 includes means for the user to set the magnitude value at which the second alarm 38 is triggered.

Referring now to FIGS. 5A-5F and 9A-9C, the probe channel itself has two branches, depending on the strength of the signal detected. Following the second filter 36, weaker signals (in the preferred embodiment, those up to 158 volts) are amplified in a first amplifier 40. This is the only difference in processing of the two levels of signals in the probe channel. It should also be noted that if, prior to use, the user has set switch SW2 so as to display the signal from the proximity detect channel, it is at this point in the probe channel that the signal from the proximity detect channel would be fed into the probe channel.

Weaker signals are passed through a second absolute value detector 42 and a first voltage follower buffer 44. Depending on the detected strength of the input signal, one or more LED's will be activated on the voltage indicator 1016. Stronger signals activate more LED's. The voltage values represented by the LED's are logarithmic in nature as opposed to linearly increasing. This enables the electrometer 10 to display outputs representing a far wider range of input voltages than would be possible with a linear display.

Returning to the output of the second filter 36, signals strong enough to activate the second branch of the probe channel are passed through a third absolute value detector 46 and a second voltage follower buffer 48. The strength of the signal then determines the appropriate number of LED's to be displayed on the upper end of voltage indicator 1016.

A polarity detect circuit 50 is included in the device that determines whether a subject ESC is positive or negative, and activates the appropriate polarity indicator light on the electrometer front panel or on the display tower.

Figure 7B:
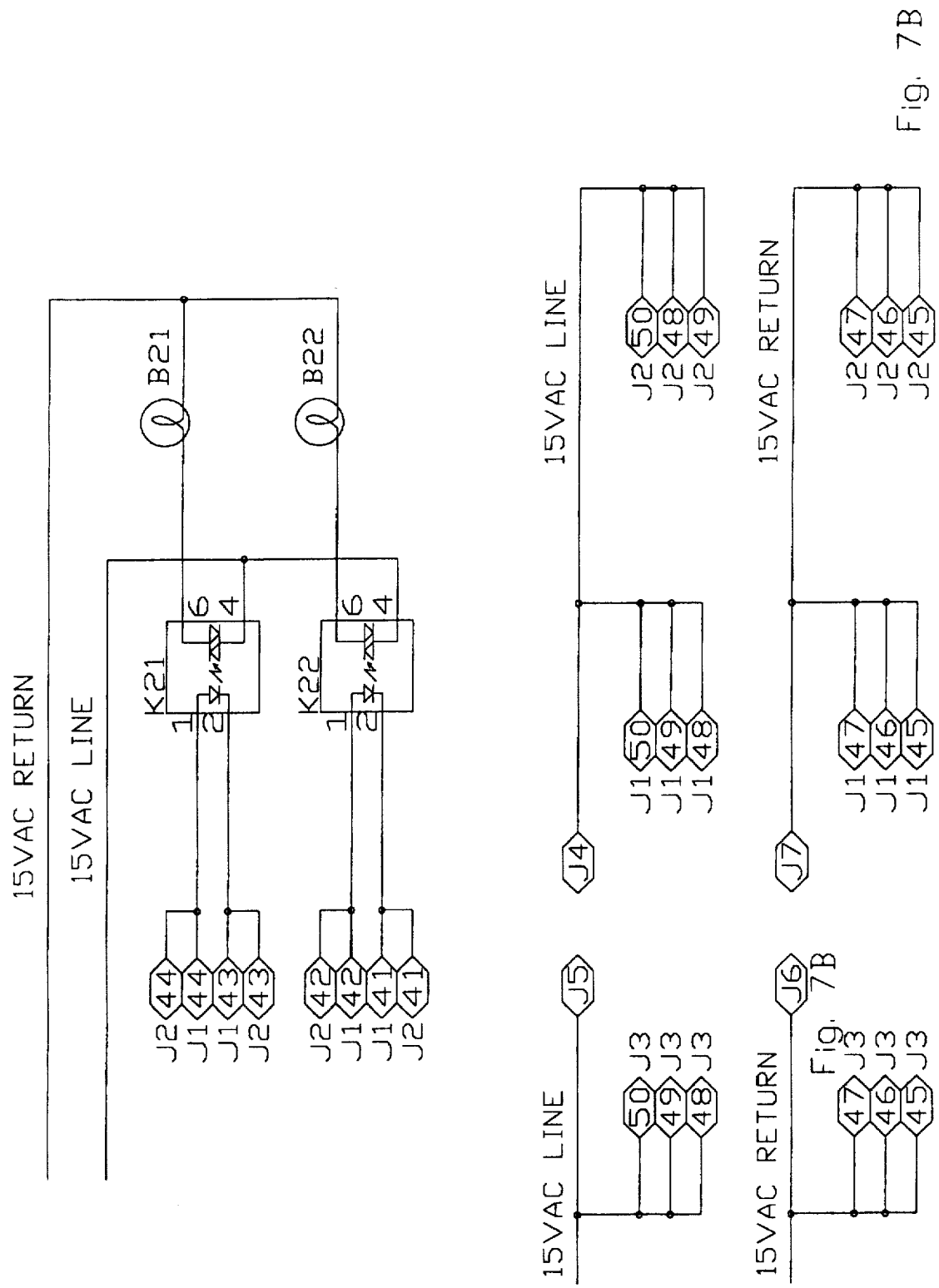
FIG. 7 is a key to FIGS. 7A–7B which comprise a circuit diagram of the display tower PCB.
Figure 8:
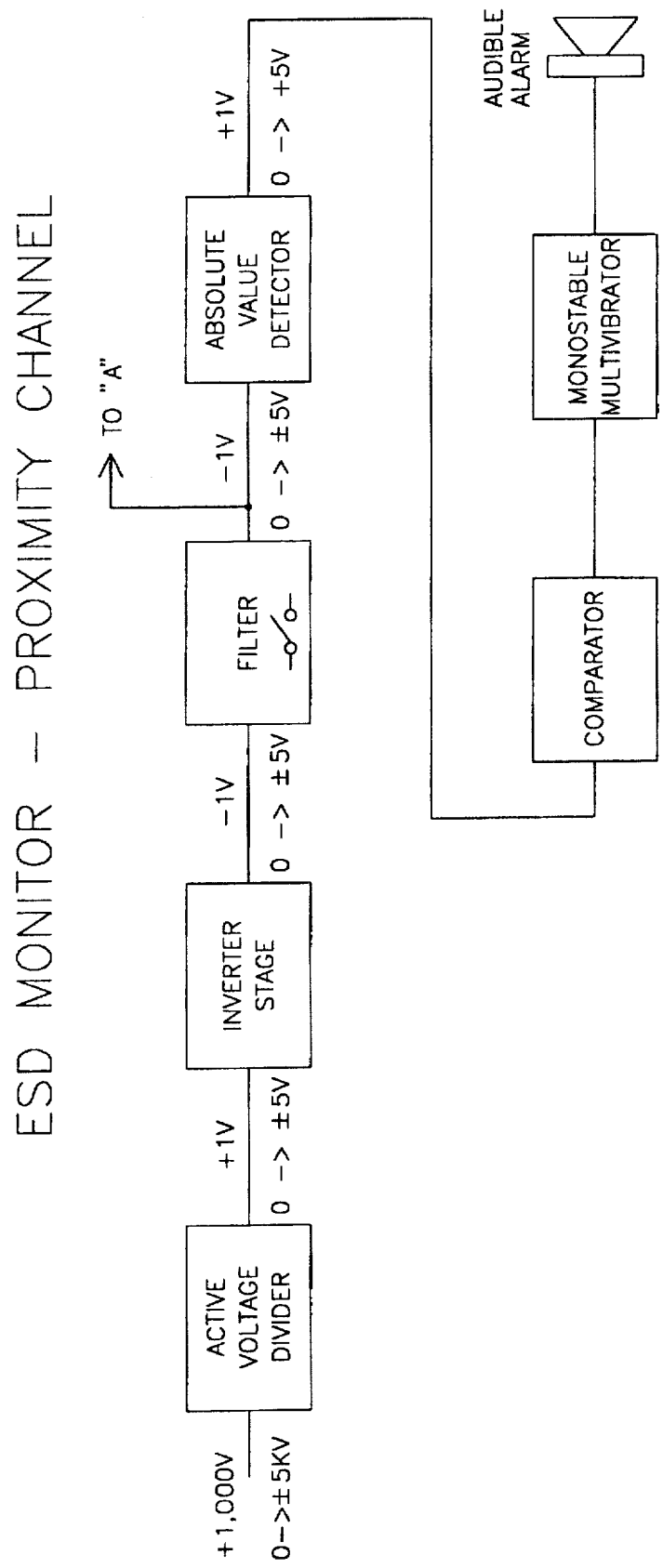
FIG. 8 is a block diagram of the proximity detect channel.
Figure 9A:
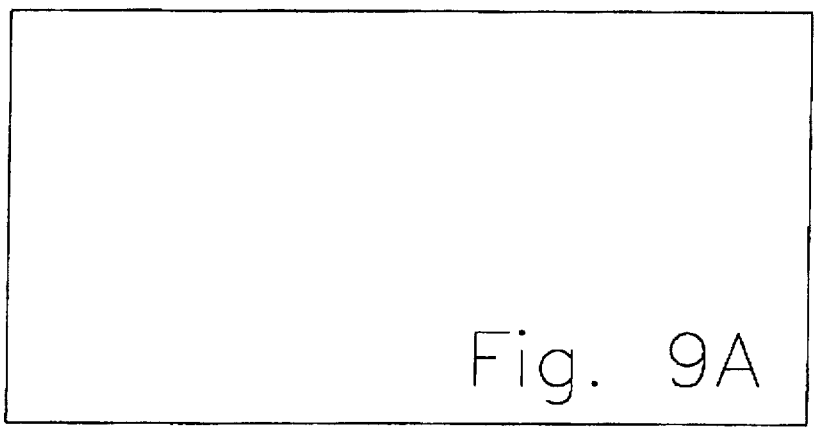
FIG. 9 is a key to FIGS. 9A–9C which comprise a block diagram of the probe channel.
Figure 9B:
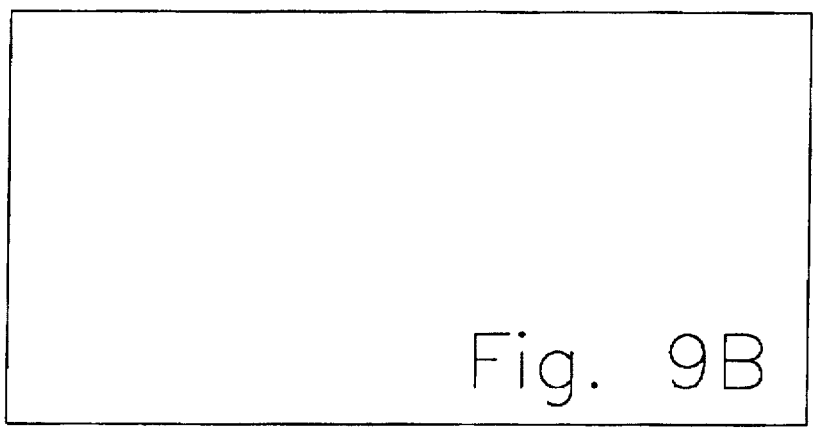
Figure 9C:
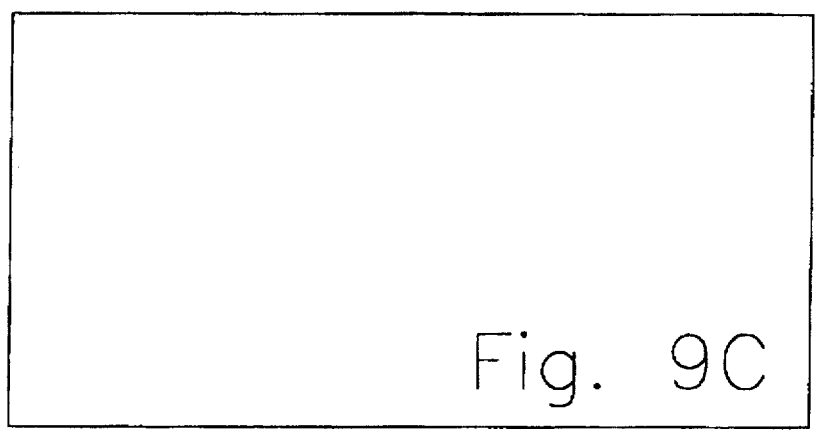
Figure 9A:
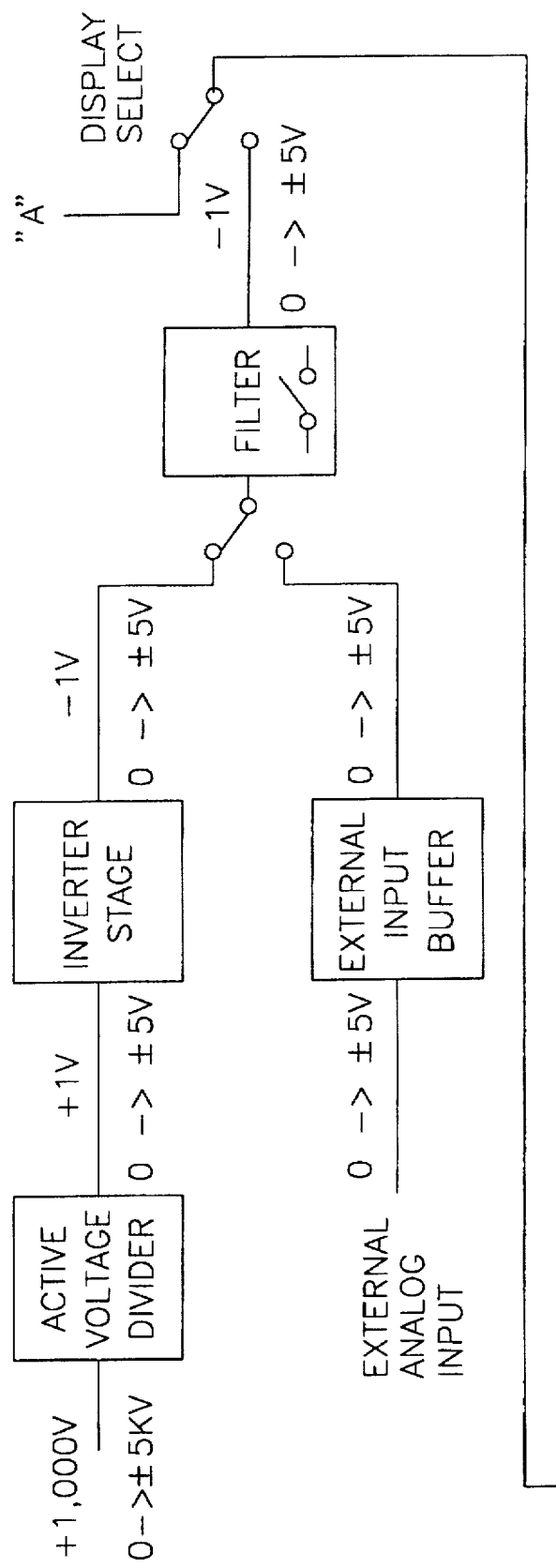
Figure 9B:
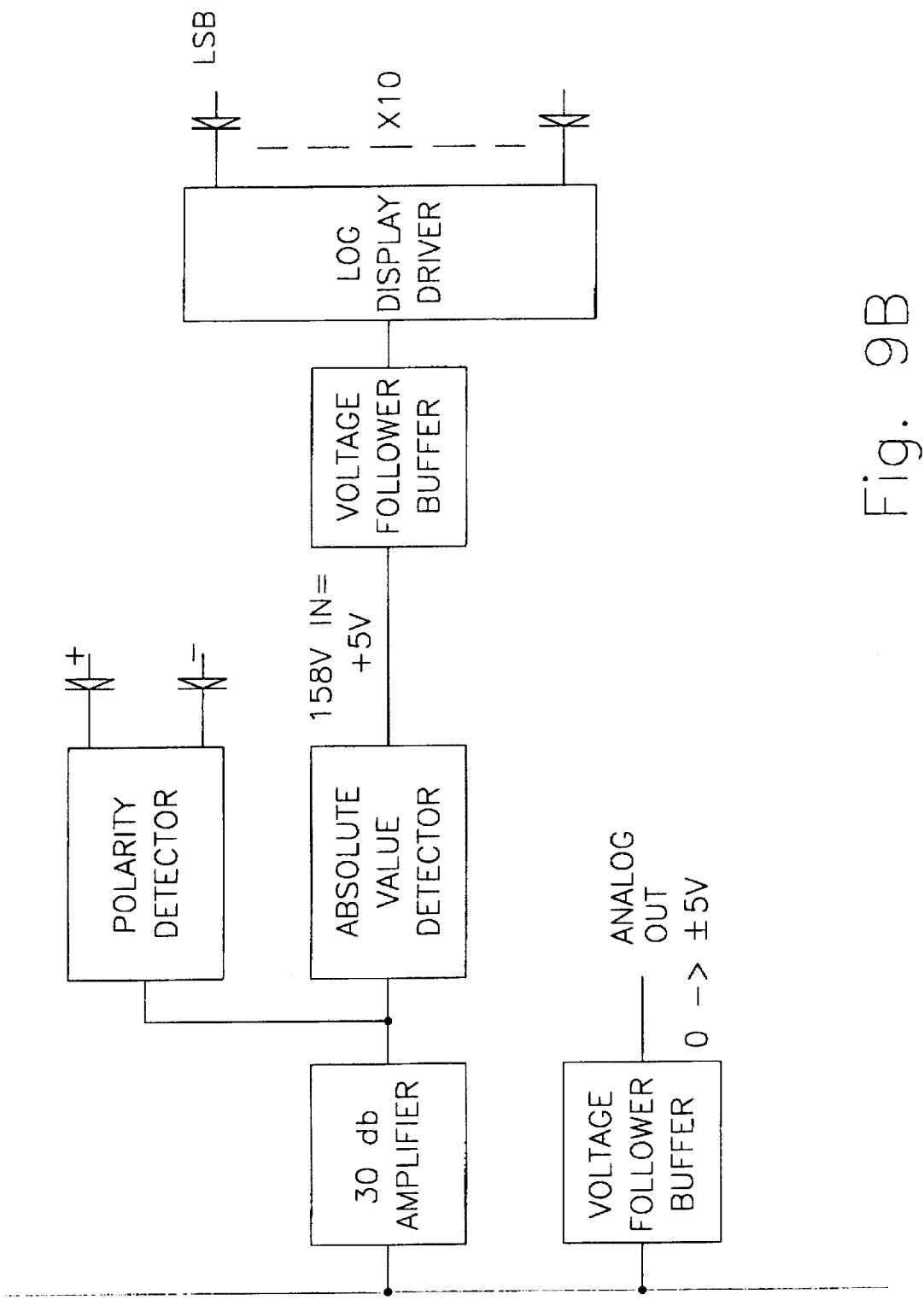
Figure 9C:
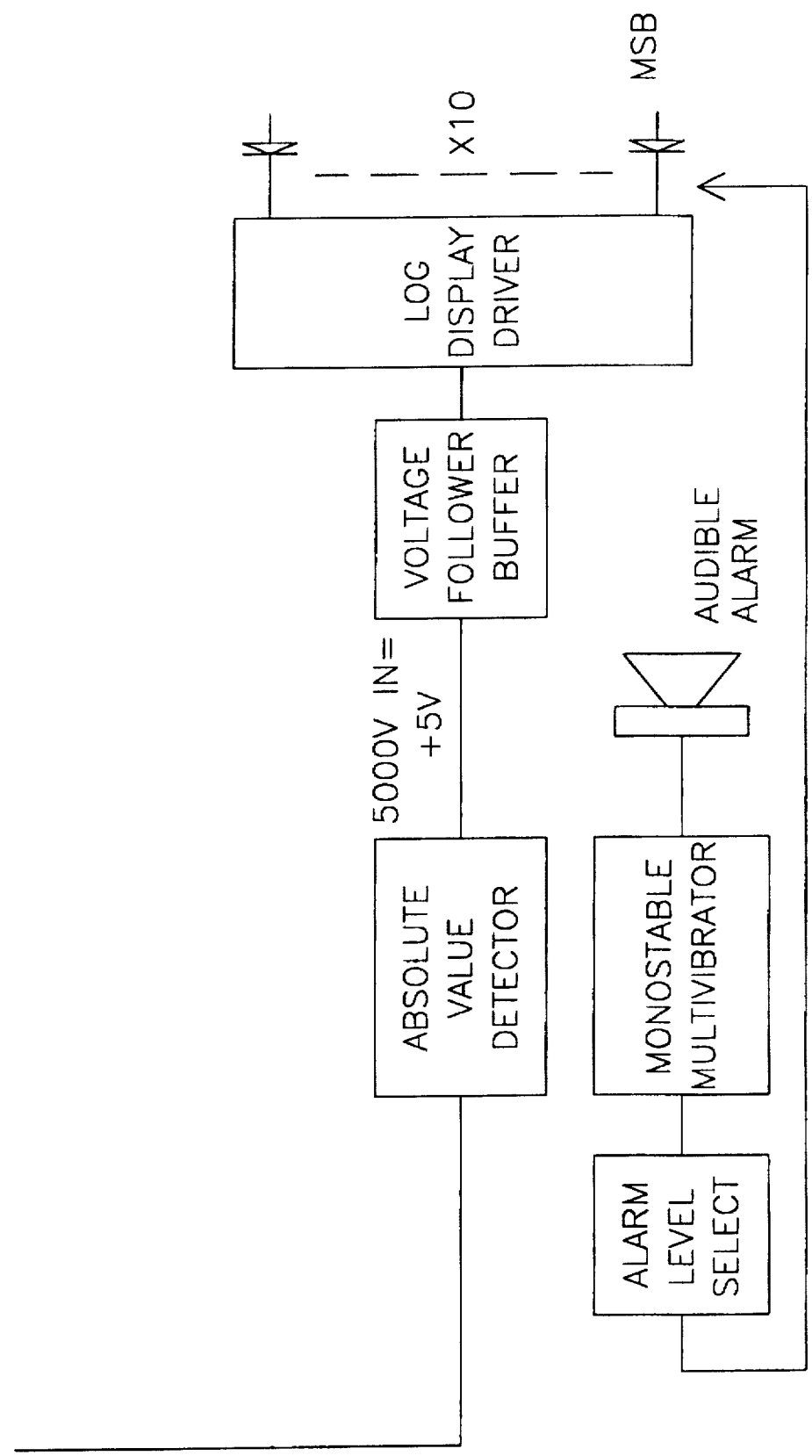
Figure 10:
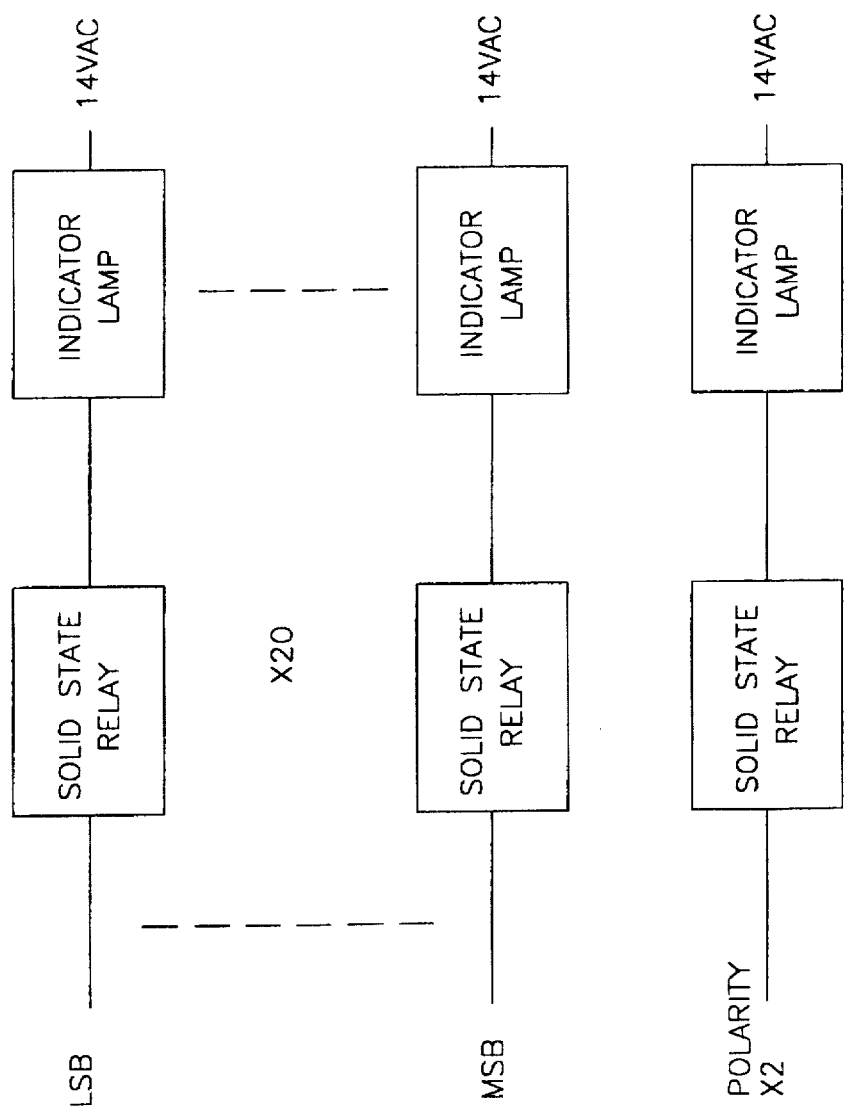
FIG. 10 is a block diagram of the peak hold option for the device.
Figure 11:
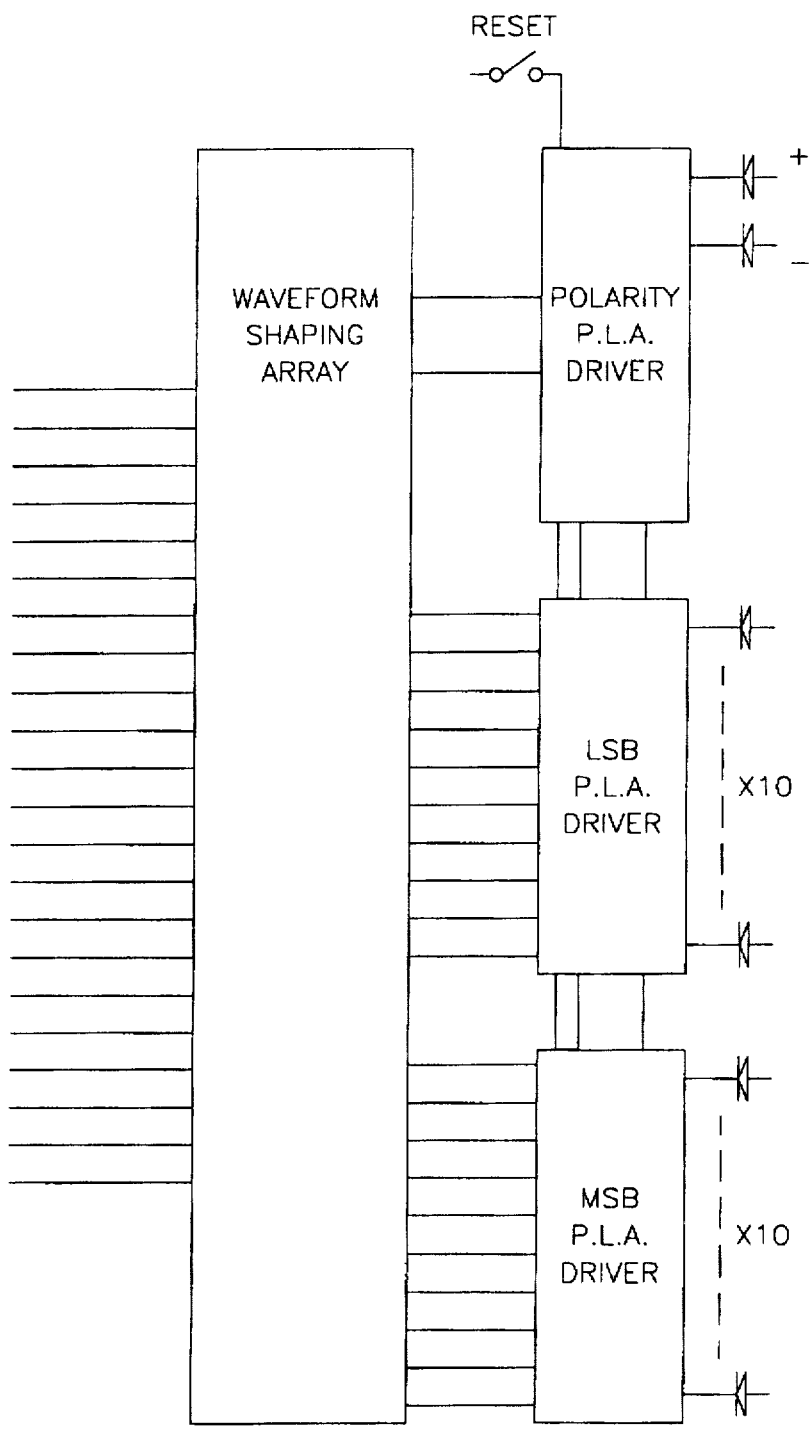
FIG. 11 is a block diagram of the display tower.

When the user so desires, the detected voltages' magnitude and polarity can be shown on the display tower 12. FIGS. 7A-7B, and 10 illustrate the additional circuitry required for the display tower. The display tower essentially transfers the values used to illuminate the displays on the face of the electrometer to larger bulbs to enhance the visual effect. The display tower 12 will generally be used in training situations.

The electrometer also includes an option for a peak hold display means, as illustrated in FIGS. 6A-6D and 11. This option allows the user to display the magnitude and polarity of the highest voltage detected during a given monitoring period. The high voltage and polarity detected remains illuminated until a higher voltage or equal voltage with reverse polarity is detected or until the session is terminated.

The above disclosure is not intended as limiting. Those skilled in the art will readily observe that numerous modifications and alterations of the device may be made while retaining the teachings of the invention. Accordingly, the above disclosure should be construed as limited only by the restrictions of the appended claims.

We claim:

1. An electrometer comprising:
   a first input channel termed a proximity detect channel,
   a second input channel termed a probe channel,
   a means to display a voltage detected by said electrometer; wherein
   inputs to said two input channels are attenuated respectively by a first active voltage divider and a second active voltage divider, said active voltage dividers are constructed to give said electrometer an extremely high input impedance on the order of 100 gigohms, thereby allowing said electrometer to measure an ESC without causing a rapid discharge.

2. The electrometer of claim 1 wherein:
   the active voltage dividers utilize an op amp in a configuration such that input voltage is attenuated rather than amplified, said configuration including a first resistor, a second resistor, and said op amp; wherein
   said first resistor has a first electrical contact with an inverting input terminal of said op amp, said first resistor has a second electrical contact with an output terminal of said op amp
   said second resistor is in the input path to said inverting input terminal of said op amp, such that the attenuation achieved by said active voltage dividers is equal to a ratio of said first resistor to said second resistor.

3. The electrometer of claim 2 wherein:
   said ratio of said first resistor to said second resistor is on the order of 0.001.

4. The electrometer of claim 3 wherein:
   a value of said first resistor is on the order of 100 megohms, and a value of said second resistor is on the order of 100,000 megohms.

5. The electrometer of claim 1 wherein:
   said proximity detect channel further includes an inverter stage, a filter, an absolute value detector, a comparator, and an alarm.

6. The electrometer of claim 1 wherein:
   said probe channel further includes an inverter stage and a filter, an output of said filter being processed through a first low voltage branch or a second high voltage branch depending on the magnitude of said output from said filter;
   said first branch further includes an amplifier, an absolute value detector, a voltage follower buffer, an LED display driver, an alarm level select, and an alarm;
   said second branch further includes an absolute value detector, a voltage follower buffer, an LED display driver, an alarm level select, and an alarm.

7. The electrometer of claim 1 wherein:

said electrometer includes means to determine and display the polarity of a measured voltage.

8. The electrometer of claim 1 wherein:

said electrometer includes a display tower with incandescent light bulbs to indicate magnitude and polarity of measured voltages.

9. The electrometer of claim 1 wherein:

said electrometer includes a series of LED's that are illuminated in proportion to a peak voltage detected by said electrometer.

10. The electrometer of claim 1 wherein:

said electrometer includes a means to receive input from independent instruments.

11. The electrometer of claim 1 wherein:

said electrometer includes a means to transmit measured values to a recording device.

12. The electrometer of claim 1 wherein:

said electrometer includes means to select an alarm threshold for said probe channel, and means to select an alarm threshold for said proximity detect channel.

13. The electrometer of claim 1 wherein:

said electrometer includes a probe means remote from a main body of said electrometer.

14. The electrometer of claim 1 wherein:

said means to display said voltage detected by said electrometer is a first series of LED's, a number of said LED's in said first series that is illuminated at a given time is proportional to a magnitude of said voltage detected.

15. An electrometer comprising:

a first input channel termed a proximity detect channel, a second input channel termed a probe channel, a means to display a voltage detected by said electrometer; wherein inputs to said two input channels are attenuated respectively by a first active voltage divider and a second active voltage divider, said active voltage dividers are constructed to give said electrometer an extremely high input impedance on the order of 100 gigohms, thereby allowing said electrometer to measure an ESC without causing a rapid discharge, the active voltage dividers utilizing an op amp in a configuration such that input voltage is attenuated rather than amplified, said configuration including a first resistor, a second resistor, and said op amp; wherein said first resistor has a first electrical contact with an inverting input terminal of said op amp, said first resistor has a second electrical contact with an output terminal of said op amp, said second resistor is in the input path to said inverting input terminal of said op amp, such that the attenuation achieved by said active voltage dividers is equal to a ratio of said first resistor to said second resistor.

16. The electrometer of claim 15 wherein:

a value of said first resistor is on the order of 100 megohms, and a value of said second resistor is on the order of 100,000 megohms.

17. The electrometer of claim 15 wherein:

said proximity detect channel further includes in electrical communication with a first one of said active voltage dividers an inverter stage, a filter, an absolute value detector, a comparator, and an alarm.

18. The electrometer of claim 15 wherein:

said probe channel further includes in electrical communication with a first one of said active voltage dividers an inverter stage and a filter, an output of said filter being processed through a first low voltage branch or a second high voltage branch depending on the magnitude of said output from said filter;

said first branch further includes an amplifier, an absolute value detector, a voltage follower buffer, an LED display driver, an alarm level select, and an alarm;

said second branch further includes an absolute value detector, a voltage follower buffer, an LED display driver, an alarm level select, and an alarm.

19. The electrometer of claim 15 wherein:

said electrometer includes in electrical communication with at least one of said input channels a means to determine the polarity of a measured voltage.

20. The electrometer of claim 15 wherein:

said electrometer includes in electrical communication with at least one of said input channels a display tower with incandescent light bulbs to indicate magnitude and polarity of measured voltages.

21. The electrometer of claim 15 wherein:

said electrometer includes a series of LED's a number of said LED's in said series that is illuminated at a given time is proportional to a magnitude of a peak voltage detected by said electrometer.

22. The electrometer of claim 15 wherein:

said electrometer includes a means to receive input from independent instruments.

23. The electrometer of claim 15 wherein:

said electrometer includes a means to transmit measured values to a recording device.

24. The electrometer of claim 15 wherein:

said electrometer includes a means in electrical communication with said probe channel to select an alarm threshold for said probe channel, and means in electrical communication with said proximity detect channel to select an alarm threshold for said proximity detect channel.

25. The electrometer of claim 15 wherein:

said electrometer includes a probe means remote from a main body of said electrometer, said probe means providing input to said probe channel.

26. The electrometer of claim 15 wherein:

said ratio of said first resistor to said second resistor is on the order of 0.001.

27. The electrometer of claim 15 wherein:

said means to display said voltage detected by said electrometer is a first series of LED's, a number of said LED's in said first series that is illuminated at a given time is proportional to a magnitude of said voltage detected.

* * * * *

UNITED STATES PATENT AND TRADEMARK OFFICE
CERTIFICATE OF CORRECTION

PATENT NO. : 5,719,502
DATED : February 17, 1998
INVENTOR(S) : Verbiest, et. al.

It is certified that error appears in the above-identified patent and that said Letters Patent is hereby corrected as shown below:

On the cover page, item 73, Assignee, please delete "Noux Corporation", and insert --NOVX Corporation--.

Signed and Sealed this

Nineteenth Day of May, 1998

Attest:

BRUCE LEHMAN

Attesting Officer

Commissioner of Patents and Trademarks